United States Patent
Shimizu et al.

(10) Patent No.: US 10,166,016 B2
(45) Date of Patent: Jan. 1, 2019

(54) MEDICAL RETRACTOR

(71) Applicants: Yusuke Shimizu, Okinawa (JP); YASUI CO., LTD., Miyazaki (JP)

(72) Inventors: Yusuke Shimizu, Okinawa (JP); Satoshi Matsuta, Miyazaki (JP); Go Aradono, Miyazaki (JP)

(73) Assignees: Yusuke Shimizu, Okinawa (JP); YASUI CO., LTD., Miyazaki (JP)

(*) Notice: Subject to any disclaimer, the term of this patent is extended or adjusted under 35 U.S.C. 154(b) by 0 days.

(21) Appl. No.: 15/327,215

(22) PCT Filed: Jun. 25, 2015

(86) PCT No.: PCT/JP2015/068331
§ 371 (c)(1),
(2) Date: Jan. 18, 2017

(87) PCT Pub. No.: WO2016/038981
PCT Pub. Date: Mar. 17, 2016

(65) Prior Publication Data
US 2017/0172555 A1    Jun. 22, 2017

(30) Foreign Application Priority Data
Sep. 13, 2014  (JP) .................. 2014-187131

(51) Int. Cl.
*A61B 1/32* (2006.01)
*A61B 17/02* (2006.01)
(Continued)

(52) U.S. Cl.
CPC ............. *A61B 17/02* (2013.01); *A61B 1/06* (2013.01); *A61B 1/32* (2013.01); *A61B 90/30* (2016.02);
(Continued)

(58) Field of Classification Search
CPC ........... A61B 2017/00907; A61B 90/30; A61B 17/02
See application file for complete search history.

(56) References Cited

U.S. PATENT DOCUMENTS 4,562,832 A * 1/1986 Wilder ................. A61B 1/32
138/DIG. 8
5,005,108 A * 4/1991 Pristash .............. G02B 6/0005
362/23.15
(Continued)

FOREIGN PATENT DOCUMENTS

EP          0808606 A1    11/1997
JP          48-003440 B    1/1973
(Continued)

OTHER PUBLICATIONS

Notification of Reasons for Refusal dated Oct. 3, 2017 from the corresponding Japanese Patent Application No. JP 2016-547745 and English translation.
(Continued)

*Primary Examiner* — Jan Christopher Merene
(74) *Attorney, Agent, or Firm* — Lucas & Mercanti, LLP

(57) ABSTRACT

Provided is a medical retractor capable of ensuring visibility in a field of operation and in the periphery of the field of operation while realizing the reduction of weight of the retractor compared to a conventional steel-made retractor. A medical retractor includes: a grip portion; and a resin functional portion made of a transparent resin and extending from the grip portion. The resin functional portion has: a trunk portion which has a proximal end thereof connected to the grip portion; and a hook-shaped portion extending in a hook shape from a distal end of the trunk portion. The resin functional portion is configured to allow the viewing of an affected part which opposedly faces a back surface of the
(Continued)

resin functional portion from a front surface side in a see-through manner.

10 Claims, 24 Drawing Sheets

(51) Int. Cl.
    *A61B 1/06*     (2006.01)
    *A61B 90/30*    (2016.01)
    *A61B 17/00*    (2006.01)

(52) U.S. Cl.
    CPC ........... *A61B 2017/0046* (2013.01); *A61B 2017/00473* (2013.01); *A61B 2017/00734* (2013.01); *A61B 2017/00907* (2013.01); *A61B 2090/304* (2016.02); *A61B 2090/306* (2016.02); *A61B 2090/308* (2016.02)

(56) References Cited

U.S. PATENT DOCUMENTS

| | | | | |
|---|---|---|---|---|
| 5,562,619 | A * | 10/1996 | Mirarchi | A61B 17/221 604/264 |
| 6,176,824 | B1 * | 1/2001 | Davis | A61B 1/24 600/178 |
| 7,049,380 | B1 * | 5/2006 | Chang | C08F 214/18 526/206 |
| 8,105,335 | B1 * | 1/2012 | Bentley | A61B 17/22 604/106 |
| 8,495,999 | B2 | 7/2013 | Law et al. | |
| 9,844,364 | B2 * | 12/2017 | Grey | A61B 17/02 |
| 2005/0171408 | A1 | 8/2005 | Parker | |
| 2006/0058779 | A1 * | 3/2006 | Broukhim | A61B 17/02 606/27 |
| 2007/0083086 | A1 | 4/2007 | LeVahn et al. | |
| 2007/0208226 | A1 * | 9/2007 | Grey | A61B 17/02 600/212 |
| 2008/0096165 | A1 | 4/2008 | Virnicchi et al. | |
| 2008/0319290 | A1 | 12/2008 | Mao et al. | |
| 2011/0028792 | A1 * | 2/2011 | Ibrahim | A61B 17/02 600/205 |
| 2012/0149992 | A1 * | 6/2012 | Duggal | A61B 17/02 600/245 |
| 2014/0012090 | A1 * | 1/2014 | Heitland | A61B 17/02 600/217 |
| 2015/0290414 | A1 * | 10/2015 | Vasan | A61M 16/0488 600/191 |
| 2016/0353978 | A1 * | 12/2016 | Miller | A61B 1/00096 |
| 2017/0224200 | A1 * | 8/2017 | Uesugi | A61B 1/00147 |
| 2017/0303779 | A1 * | 10/2017 | Law | A61M 16/0488 |

FOREIGN PATENT DOCUMENTS

| | | |
|---|---|---|
| JP | H10277043 A | 10/1998 |
| JP | 2001-212150 A | 8/2001 |
| JP | 2001327525 A | 11/2001 |
| JP | 2002524182 A | 8/2002 |
| JP | 2008-500112 A | 1/2008 |
| JP | 2009523551 A | 6/2009 |
| JP | 2009268763 A | 11/2009 |
| JP | 2012500043 A | 1/2012 |
| JP | 2013006094 A | 1/2013 |
| JP | 2013500066 A | 1/2013 |
| JP | 2015037610 A | 2/2015 |
| JP | 2015042281 A | 3/2015 |
| WO | 03/075979 A2 | 9/2003 |
| WO | 2005/115223 A2 | 12/2005 |
| WO | 2007084641 A2 | 7/2007 |
| WO | 2009/095451 A1 | 8/2009 |
| WO | 2012045459 A1 | 4/2012 |

OTHER PUBLICATIONS

International Search Report dated Sep. 15, 2015 for PCT/JP2015/068331 and English translation.

Supplementrt Partial European Search Report dated Mar. 29, 2018 from the corresponding European Patent Application No. EP 15839219.1.

Extended European Search Report dated Aug. 30, 2018 from corresponding European Application No. 15839219.1.

* cited by examiner (a)

(b) ENLARGED CROSS-SECTIONAL VIEW TAKEN ALONG LINE A-A (c) ENLARGED CROSS-SECTIONAL VIEW TAKEN ALONG LINE B-B (a)

(b) ENLARGED CROSS-SECTIONAL VIEW TAKEN ALONG LINE P-P (c) ENLARGED CROSS-SECTIONAL VIEW TAKEN ALONG LINE Q-Q (a)

(b) ENLARGED CROSS-SECTIONAL VIEW TAKEN ALONG LINE D-D (c) ENLARGED CROSS-SECTIONAL VIEW TAKEN ALONG LINE E-E (a)

(b) ENLARGED CROSS-SECTIONAL VIEW TAKEN ALONG LINE F-F (c) ENLARGED CROSS-SECTIONAL VIEW TAKEN ALONG LINE G-G (a)

(b) ENLARGED CROSS-SECTIONAL VIEW TAKEN ALONG LINE H-H (c)

(c) ENLARGED CROSS-SECTIONAL VIEW TAKEN ALONG LINE K-K (a)

(b)

(a)

(b) ENLARGED CROSS-SECTIONAL VIEW TAKEN ALONG LINE M-M (a)

(b) ENLARGED CROSS-SECTIONAL VIEW TAKEN ALONG LINE N-N

MEDICAL RETRACTOR

CROSS REFERENCE TO RELATED APPLICATION

This Application is a 371 of PCT/JP2015/068331 filed on Jun. 25, 2015, which, in turn, claimed the priority of Japanese Patent Application No. 2014-187131 filed on Sep. 13, 2014, both applications are incorporated herein by reference.

TECHNICAL FIELD

The present invention relates to a medical retractor.

BACKGROUND ART

Currently, various steel-made utensils are used in medical field. "steel-made utensil" means an instrument for operations made of metal such as stainless steel. Steel-made utensils include tweezers, needle holders, scalpels, scissors, forceps, wound retractors, chisels, cupped forceps and the like. Kinds of such steel-made utensils amount to approximately 30, and there are several hundred variations in shapes of distal ends and sizes of these steel-made utensils. Being made of metal, these steel-made utensils have advantages and disadvantages.

For example, as one of steel-made wound retractors, to facilitate the viewing of the center of field of operation, there has been used an instrument called a retractor which retracts a peripheral tissue by hooking by a hook-shaped portion formed on a distal end of the retractor. With respect to this metal-made retractor, patent document 1 points out various drawbacks.

That is, as the drawbacks of a metal-made retractor, the following drawbacks are pointed out. A metal-made retractor is heavy and hence, a large burden is placed on a user's hand. A metal-made retractor is heavy and hence, a large-sized metal-made retractor cannot be manufactured. A flash of light is generated under high level illumination due to reflection of the light. Since a metal-made retractor has high thermal conductivity, the metal-made retractor rapidly absorbs heat from a tissue of an affected part thus giving rise to a possibility that the patient suffers from a heat shock. Since metal-made retractors are expensive, the inventory of retractors at facilities in a hospital is liable to be constantly insufficient.

To overcome such drawbacks which a steel-made utensil has, patent document 1 proposes a retractor for operations which includes constitutional elements consisting of: an integrally-formed blade which has a non-reflective surface and is made of an elastic and strong plastic material; a grip; and a shank which connects the grip and the blade to each other.

Further, as drawbacks in medical field, patent document 2 points out drawbacks brought about by a shortage of illumination, a shortage of reflection or the like in a field of operation.

To overcome the drawbacks relating to the illumination, patent document 2 proposes a medical wound retractor illumination system where a light source is mounted on a removable handle portion of a wound retractor, and light incident through an incident port formed in a portion of the wound retractor near the handle is emitted toward a field of operation existing near a blade portion remote from the handle through a light guide in the wound retractor.

PRIOR ART LITERATURE

Patent Literature

[Patent document 1] Japanese Examined Patent Application Publication No. 48-3440
[Patent document 2] Japanese Translation of PCT International Publication No. JP-T-2009-523551

SUMMARY OF THE INVENTION

Technical Problem

However, the steel-made utensils have various other drawbacks besides the above-mentioned drawbacks. For example, when a medical operating instrument is disposed on the periphery of a field of operation, the instrument shields the field of operation and the periphery of the field of operation so that visibility of the field of operation and the periphery of the field of operation is lowered thus obstructing an operation. To be more specific, with respect to an operation target part located in a deep part of a human body, it is necessary to change a degree of incision between a superficial layer tissue and a deep layer tissue and hence, it is necessary to use both a first wound retractor which retracts a tissue on a superficial layer side and a second wound retractor which retracts a tissue on a deep layer side at the same time. In this case, there is a possibility that a tissue incised by the first wound retractor is shielded by the second wound retractor and this shielding of the tissue is one of factors which lower the visibility of the field of operation.

This drawback relating to visibility of a field of operation has a possibility of becoming conspicuous with the plastic-made wound retractor disclosed in above-mentioned patent literature 1 when compared to a metal-made wound retractor. That is, plastic is inferior to metal in strength and hence, to enable a plastic-made wound retractor to acquire a strength equivalent to a strength of a steel-made wound retractor, a size of the plastic wound retractor is liable to become larger and hence, there is a high possibility that visibility of a field of operation is lowered compared to a case where a metal-made wound retractor is used.

The present invention has been made in view of such circumstances, and it is an object of the present invention to provide a medical retractor capable of ensuring visibility of a field of operation and in the periphery of the field of operation while realizing the reduction of weight of the retractor compared to a conventional steel-made retractor. It is another object of the present invention to provide a medical retractor capable of enhancing visibility of a field of operation and in the periphery of the field of operation compared to a conventional steel-made retractor.

Solution to Problem

According to one aspect of the present invention, there is provided a medical retractor which includes: a grip portion; and a resin functional portion made of a transparent resin and extending from the grip portion, wherein the resin functional portion has: a trunk portion which has a proximal end thereof connected to the grip portion; and a hook-shaped portion extending in a hook shape from a distal end of the trunk portion, and the resin functional portion is configured to allow the viewing of an affected part which oppsedly faces a back surface of the resin functional portion from a front surface side in a see-through manner.

According to the medical retractor having such a configuration, an affected part which opposedly faces the back surface side of the resin functional portion is viewable through the hook-shaped portion. Accordingly, an affected part which is disposed in a shadow of the hook-shaped portion and is not viewable if the medical retractor is formed of a steel-made retractor is viewable and hence, visibility of a field of operation can be largely increased compared to a conventional steel-made retractor. Also with respect to the trunk portion, an affected part which opposedly faces the back surface side is viewable and hence, even when a first retractor which retracts a tissue on a superficial layer side and a second retractor which retracts a tissue on a deep layer side are used simultaneously, it is possible to view the tissue which is retracted by the first retractor and is positioned on a back side of the second retractor through the trunk portion of the second retractor. Accordingly, visibility of a field of operation can be enhanced compared to the conventional medical retractor.

According to one of selective aspects of the present invention, the grip portion incorporates a light source which emits light by means of a power source therein such that the light from the light source is incident on a proximal end of the trunk portion and is transmitted toward the hook-shaped portion whereby visibility of a tissue of an affected part which opposedly faces a back surface of the resin functional portion from a front surface side of the resin functional portion is enhanced.

With such a medical retractor, not to mention that light which is incident on the proximal end of the trunk portion from the light source of the grip portion is emitted from the distal ends and corner portions of the hook-shaped portion and the like and is irradiated to a tissue of an affected part in the periphery of the medical retractor, leaked light is generated from a wall surface parallel to an advancing direction of light and hence, it is possible to largely increase visibility of a tissue of an affected part which opposedly faces such a wall surface (back surface) when viewed from a wall surface (front surface) on a side opposite to the affected part.

According to one of selective aspects of the present invention, in the grip portion, a communication passage between a fixing hole in which the resin functional portion is fixed and an accommodating space in which the light source is accommodated are sealed by a sealing material.

With such a medical retractor, it is possible to prevent a possibility that a liquid (body fluid, drug solution or the like) which has a possibility of being fixed to a connecting portion between the grip portion and the resin functional portion during an operation intrudes into the inside of the grip portion through a gap in the connecting portion. Accordingly, it is possible to eliminate lowering of light emitting intensity of the light source and short-circuiting of an inner electric system.

According to one of selective aspects of the present invention, the resin functional portion includes a layered structure where layers are stacked so as to have a layer boundary along an extending direction of the trunk portion.

With such a medical retractor, light which is incident on the resin functional portion from the light source minimally leaks to the outside due to an effect of closing light in the layer boundary and hence, a quantity of light which reaches the hook-shaped portion extending from the distal end of the trunk portion can be increased. Further, by selecting a direction approximately orthogonal to the back surface of the resin functional portion as the direction of the layer boundary, it is possible to ensure leaked light to the back surface side at the same level or above corresponding leaked light when a resin functional portion does not have the layered structure and hence, it is possible to prevent lowering of an effect of enhancing back-surface-side visibility by leaked light.

According to one of selective aspects of the present invention, the back surface and the front surface of the resin functional portion are respectively formed of a flat surface.

With such a medical retractor, the back surface and the front surface of the resin functional portion are respectively formed flat and hence, it is possible to ensure favorable visibility of an affected part which opposedly faces the back surface as viewed from a front surface side. Further, it is possible to view the affected part in an actual size.

According to one of selective aspects of the present invention, the resin functional portion is configured such that at least one of the back surface and the front surface has a convex lens shape.

With such a medical retractor, an affected part which opposedly faces the back surface is viewed in an enlarged state from a front surface side and hence, while ensuring visibility of the affected part which opposedly faces the back surface of the resin functional portion from the front surface side, it is also possible to view a fine part of a tissue of the affected part.

According to one of selective aspects of the present invention, at least one of water repellant finish or oil repellant finish is applied to a surface of the resin functional portion.

With such a medical retractor, an aqueous liquid or an oil-based liquid minimally adheres to the surface of the resin functional portion so that it is possible to prevent as much as possible a case where visibility and light emission through the resin functional portion are lowered by a liquid which has a possibility of being adhered to the resin functional portion during an operation.

According to one of selective aspects of the present invention, a portion of the hook-shaped portion is formed of a light storage member.

With such a medical retractor, it is possible to make a portion of the medical retractor emit light even when the medical retractor is not provided with a light source. Further, even in the case where the medical retractor is provided with a light source, when light emission from the light source is stopped due to a power source condition, the light storage member emits light for a fixed time and hence, a field of vision can be maintained to some extent in a field of operation.

According to one of selective aspects of the present invention, a prism structure which makes light refract and advance is disposed on a bent portion between the trunk portion and the hook-shaped portion.

With such a medical retractor, light which advances through the trunk portion can easily advance toward the hook portion without being emitted to the outside at the bent portion. Accordingly, a quantity of light irradiated to a field of operation around the hook-shaped portion is increased and leaked light from the hook-shaped portion is also increased and hence, back-surface-side visibility can be enhanced.

According to one of selective aspects of the present invention, a reflection portion is formed along an outer peripheral surface of the bent portion between the trunk portion and the hook-shaped portion.

With such a medical retractor, light which advances through the trunk portion can easily advance toward the hook-shaped portion without being emitted to the outside at a bent portion. Accordingly, a quantity of light irradiated to a field of operation around the hook-shaped portion is increased and leaked light from the hook-shaped portion is also increased and hence, back-surface-side visibility can be enhanced.

According to one of selective aspects of the present invention, finger hooking structures which project sideward from side surfaces of the grip portion are provided in left and right symmetry.

With such a medical retractor, a burden imposed on a doctor or an assistant in retracting a tissue using a medical retractor can be reduced.

According to one of selective aspects of the present invention, the resin functional portion has a projection extending to the hook-shaped portion along the front surface of the resin functional portion, and the projection formed on the hook-shaped portion is formed with a larger width and a smaller projecting height compared to the projection formed in the trunk portion.

With such a medical retractor, a strength of the medical retractor is reinforced by the projection having the rib structure and hence, a resin which has low rigidity compared to metal can ensure sufficient rigidity. Further, the projecting height of the projection formed on the hook-shaped portion near an operation target part is set small and hence, shielding of a field of operation by the projection is lowered as much as possible. Further, the projection has the larger width and hence, back-surface-side visibility through the projection can be ensured to some extent.

The medical retractor described heretofore includes the medical retractor used in various modes where the medical retractor is used in a state where the medical retractor is incorporated into other equipment or in a state where the medical retractor is used in other methods.

Advantageous Effects of Invention

According to the present invention, there is provided the medical retractor capable of ensuring visibility of a field of operation and in the periphery of the field of operation while realizing the reduction in weight of the retractor compared to a conventional steel-made retractor. That is, according to the medical retractor of the present invention, an affected part which opposedly faces the back surface side of the resin functional portion is viewable through the hook-shaped portion. Accordingly, an affected part which is disposed in a shadow of the refractor and is not viewable if the medical retractor is formed of a steel-made retractor is viewable and hence, visibility of a field of operation can be largely increased compared to a conventional steel-made retractor. Also with respect to the trunk portion, an affected part which opposedly faces the back surface side is viewable and hence, even when a first retractor which retracts a tissue on a superficial layer side and a second retractor which retracts a tissue on a deep layer side are used simultaneously, it is possible to view the tissue which is retracted by the first retractor and is positioned on a back side of the second retractor through the trunk portion of the second retractor. Accordingly, visibility of a field of operation can be enhanced compared to the conventional medical retractor.

According to one embodiment of the invention, not to mention that light which is incident on the proximal end of the trunk portion from the light source of the grip portion is emitted from the distal ends and corner portions of the hook-shaped portion and the like and is irradiated to an affected part in the periphery of the medical retractor, leaked light is generated from a wall surface parallel to an advancing direction of light and hence, it is possible to largely increase visibility of an affected part which opposedly faces such a wall surface (back surface) when viewed from a wall surface (front surface) side on a side opposite to the affected part. Accordingly, the visibility of a field of operation can be enhanced compared to the prior art.

According to one embodiment of the invention, with such a medical retractor, it is possible to prevent a possibility that a liquid (body fluid, drug solution or the like) which has a possibility of being adhered to a connecting portion between the grip portion and the resin functional portion during an operation intrudes into the inside of the grip portion through a gap in the connecting portion. Accordingly, it is possible to eliminate lowering of light emitting intensity of the light source and short-circuiting of an inner electric system.

According to one embodiment of the invention, with such a medical retractor, light which is incident on the resin functional portion from the light source minimally leaks to the outside due to an effect of closing light in the layer boundary and hence, a quantity of light which reaches the hook-shaped portion extending from the distal end of the trunk portion can be increased. Further, by selecting a direction approximately orthogonal to the back surface of the resin functional portion as the direction of the layer boundary, it is possible to ensure leaked light to the back surface side at the same level or above corresponding to leaked light when a resin functional portion does not have the layered structure and hence, it is possible to prevent lowering of an effect of enhancing back-surface-side visibility by leaked light.

According to one embodiment of the invention, with such a medical retractor, the back surface and the front surface of the resin functional portion are respectively formed flat and hence, it is possible to ensure favorable visibility of an affected part which opposedly faces the back surface as viewed from a front surface side. Further, it is possible to view the affected part in an actual size.

According to one embodiment of the invention, with such a medical retractor, an affected part which opposedly faces the back surface is viewed in an enlarged state from a front surface side and hence, while ensuring visibility of the affected part which opposedly faces the back surface of the resin functional portion from the front surface side, it is also possible to view a fine part of a tissue of the affected part.

According to one embodiment of the invention, with such a medical retractor, an aqueous liquid or an oil-based liquid minimally adheres to the surface of the resin functional portion so that it is possible to prevent as much as possible a case where visibility and light emission through the resin functional portion are lowered by a liquid which has a possibility of being adhered to the resin functional portion during an operation.

According to one embodiment of the invention, with such a medical retractor, it is possible to make a portion of the medical retractor emit light even when the medical retractor is not provided with a light source. Further, even in the case where the medical retractor is provided with a light source, when light emission from the light source is stopped due to a power source condition, the light storage member emits light for a fixed time and hence, a field of vision can be maintained to some extent in a field of operation.

According to one embodiment of the invention, with such a medical retractor, light which advances through the trunk portion can easily advance toward the hook-shaped portion without being emitted to the outside at a bent portion. Accordingly, a quantity of light irradiated to a field of operation around the hook-shaped portion is increased and leaked light from the hook-shaped portion is also increased and hence, back-surface-side visibility can be enhanced.

According to one embodiment of the invention, with such a medical retractor, light which advances through the trunk portion can easily advance toward the hook-shaped portion without being emitted to the outside at a bent portion. Accordingly, a quantity of light irradiated to a field of operation around the hook-shaped portion is increased and leaked light from the hook-shaped portion is also increased and hence, back surface-side visibility can be enhanced.

According to one embodiment of the invention, with such a medical retractor, a burden imposed on a doctor or an assistant in retracting a tissue using a medical retractor can be reduced.

According to one embodiment of the invention, with such a medical retractor, a strength of the medical retractor is reinforced by the rib structure formed of the projection and hence, a resin which has low rigidity compared to metal can ensure sufficient rigidity. Further, the projecting height of the projection formed on the hook-shaped portion near an operation target part is set small and hence, shielding of a field of operation by the projection is lowered as much as possible. Further, the projection has the larger width and hence, back-surface-side visibility through the projection can be ensured to some extent.

BRIEF DESCRIPTION OF DRAWINGS

FIG. 2(a) to FIG. 2(c) are views of the medical retractor according to the first embodiment, wherein FIG. 2(a) is a side view, and FIG. 2(b) and FIG. 2(c) are cross-sectional views.

DESCRIPTION OF EMBODIMENTS

Hereinafter, the technique according to the present invention is described in accordance with the following order of the embodiments.
(1) First embodiment:
(2) Second embodiment:
(3) Third embodiment:
(4) Fourth embodiment:
(5) Fifth embodiment:
(6) Sixth embodiment:
(7) Seventh embodiment:
(8) Eighth embodiment:
(9) Other modifications:

(1) First Embodiment

Figure 1:
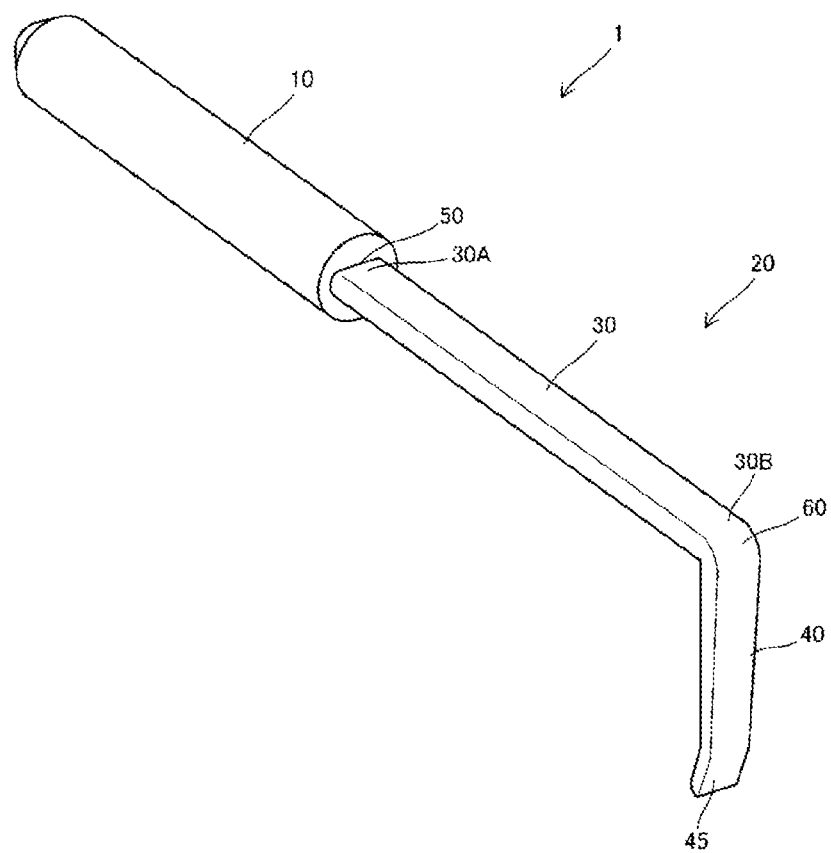
FIG. 1 is a perspective view of a medical retractor according to a first embodiment.
Figure 2:
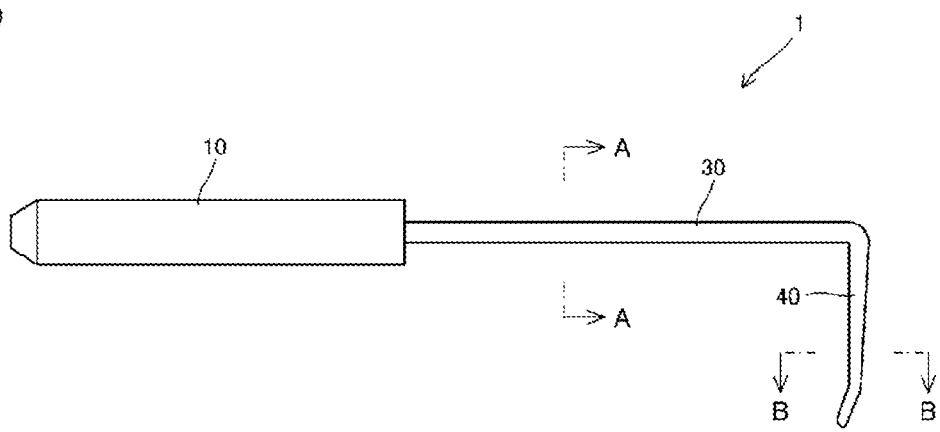
Figure 2:
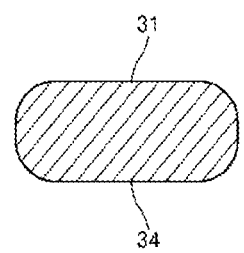
Figure 2:
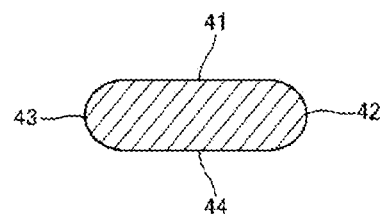
Figure 3:
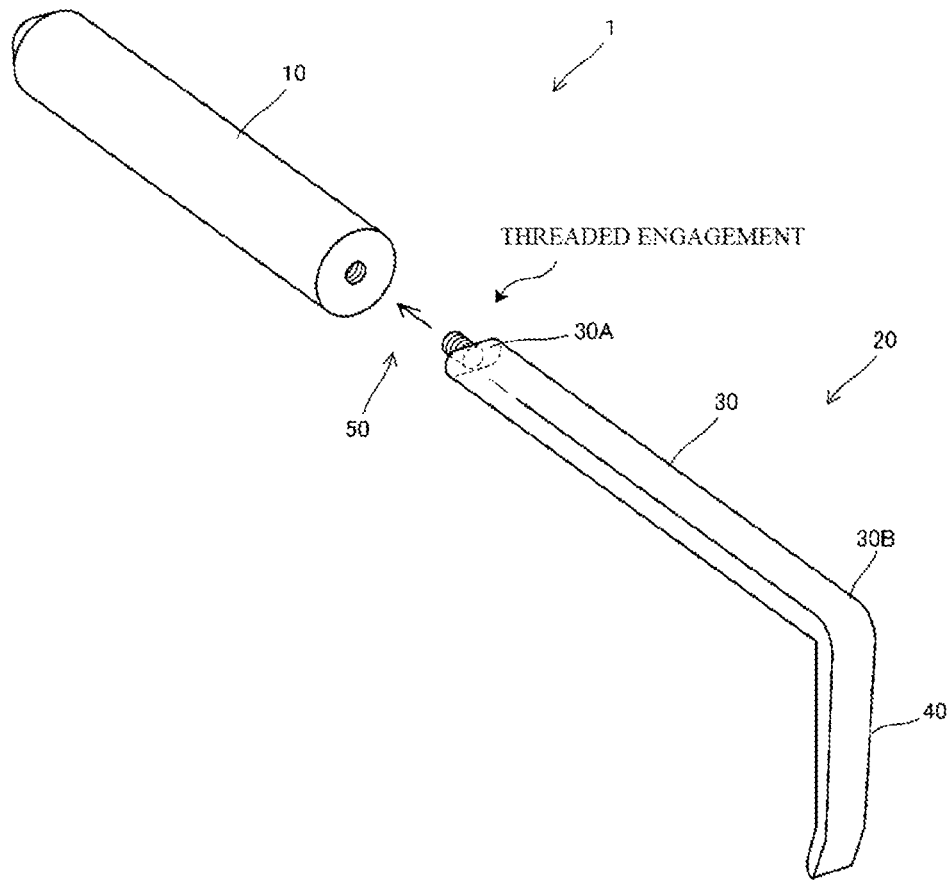
FIG. 3 is a perspective view showing a disassembled state of a connecting portion of the medical retractor according to the first embodiment.
Figure 4:
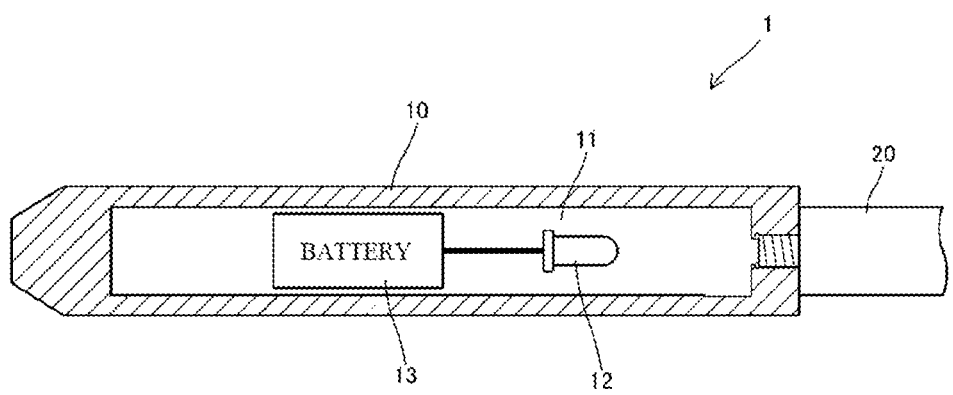
FIG. 4 is a cross-sectional view of a grip portion of the medical retractor according to the first embodiment.

FIG. 1 to FIG. 4 are views for describing a medical retractor 1 according to this embodiment. FIG. 1 is a perspective view showing the medical retractor 1, FIG. 2(a) to (c) are a side view and cross-sectional views of the medical retractor 1, FIG. 3 is a perspective view showing a disassembled state of a connecting portion of the medical retractor 1, and FIG. 4 is a cross-sectional view of a grip portion of the medical retractor 1.

In this specification, a tissue of an operation target and a part which a doctor considers it necessary to visually observe during an operation in association with the operation are referred to as "affected part", and a region including the affected part and the periphery of the affected part is referred to as "field of operation".

The medical retractor 1 includes: a grip portion 10 which a practitioner such as a doctor or an assistant holds; and a resin functional portion 20 which is used in a state where the resin functional portion 20 is connected and fixed to a distal end of the grip portion 10.

The grip portion 10 has an accommodating space 11 in which a light source 12 and a power source 13 for the light source 12 are accommodated and fixed. Although a material for forming the grip portion 10 and a shape of the grip portion 10 are not particularly limited, the grip portion 10 can be manufactured using a lightweight resin or lightweight metal, and has an outer surface shape which allows a user to acquire favorable grip performance when the user holds the grip portion 10.

For example, grip performance can be further improved by applying an anti-slip sheet to a surface of the grip portion 10 or by applying anti-slip treatment to the surface of the grip portion 10. Further, grip performance may be enhanced by adopting the following configurations. A stepped portion is formed on a connecting portion 50 between the grip portion 10 and the resin functional portion 20 in such a manner that a diameter of the stepped portion is decreased toward the resin functional portion 20 from a grip portion 10 side thus making fingers of a user more firmly engaged with the grip portion 10. Alternatively, the diameter of the grip portion 10 at a position in the vicinity of the center in the longitudinal direction of the grip portion 10 is increased.

As the light source 12, various kinds of light sources which can be accommodated in the accommodating space 11 can be adopted. For example, an LED (Light Emitting Diode), a small-sized semiconductor laser or the like can be adopted as the light source 12. It is preferable that the light source 12 be a lightweight light source. The light source 12 is fixed such that a light emitting surface of the light source 12 is directed to a distal end side of the grip portion 10 (a proximal end side of the resin functional portion 20).

As the power source 13, various kinds of batteries which can be accommodated in the accommodating space 11 can be adopted. Accordingly, a shape of the battery such as an AA-sized battery, an AAA-sized battery or a button-type battery, whether the battery is a rechargeable battery or a non-rechargeable battery, a material for forming an electrode such as manganese, lithium ion or hydrogen and the like are not particularly limited, and various type of batteries can be adopted.

An openable/closeable portion may be mounted on the accommodating space 11 so as to an exchange of the power source 13 or the light source 12. In this embodiment, a method is adopted where the light source 12 and the power source 13 are incorporated in the grip portion 10. However, it is possible to adopt a method where the power source 13 is not incorporated in the grip portion 10 or a method where neither the power source 13 nor the light source 12 is incorporated in the grip portion 10. For example, the power source 13 is formed of an external power source, and the light source 12 incorporated in the accommodating space 11 and the external power source 13 are connected to each other using a power source supply line. Further, for example, both the light source 12 and the power source 13 may be disposed outside the grip portion 10, and light emitted from the light source 12 is guided to a proximal end portion of the resin functional portion 20 using a light guide member such as optical fibers.

A distal end of the grip portion 10 and the resin functional portion 20 are fixed to each other in a detachable manner by the connecting portion 50 so as to form an integral body. In the example shown in FIG. 3 and FIG. 4, the distal end of the grip portion 10 and a proximal end of the resin functional portion 20 are fixed to each other due to fastening of a female threaded structure and a male threaded structure. With such a configuration, by releasing the fastening between the grip portion 10 and the resin functional portion 20, the resin functional portion 20 can be exchanged with a new one and the new one can be fixed to the grip portion 10, or the resin functional portion 20 can be exchanged with a resin functional portion having a different shape and such a resin functional portion can be fixed to the grip portion 10.

Between the accommodating space 11 and the connecting portion 50, a transparent partition wall structure or sealing structure is provided for preventing intrusion of a liquid (a body fluid, a drug solution and the like) into the accommodating space 11 from the outside of the connecting portion 50. The transparent partition wall structure is formed by fixing a glass material, a transparent resin material or the like by fitting or adhesion, or by integrally molding a transparent resin material with the grip portion 10. Further, when a communication passage is formed between the accommodating space 11 and the connecting portion 50, for example, the communication passage is sealed by a sealing member such as an O ring sandwiched between the distal end of the grip portion 10 and the proximal end of the resin functional portion 20.

The resin functional portion 20 includes: a trunk portion 30 which has a proximal end portion 30A thereof connected and fixed to the grip portion 10; and a hook-shaped portion 40 which extends from a distal end portion 30B of the trunk portion 30 in a state where the hook-shaped portion 40 is bent in a hook shape. The trunk portion 30 is configured such that an affected part which faces a back surface 34 of the trunk portion 30 can be viewed from a front surface 31 side of the trunk portion 30 in a see-through manner.

The resin functional portion 20 is formed of a resin material having a smooth surface with no irregularities on the surface, and has light transmissivity. Accordingly, an affected part which faces back surfaces 34, 44 can be viewed from front surface 31, 41 sides in a see-through manner.

As a material for forming the resin functional portion 20, various kinds of resin materials suitable for medical use can be adopted. As one example, polyethylene, polypropylene, polyethylene terephthalate, vinyl chloride, polystyrene, ABS, acrylic, polyamide (nylon), polycarbonate, polyacetal or the like can be named.

When a resin material has an internal strain due to a residual internal stress, it is preferable that the residual internal stress be released by applying annealing treatment or the like to the resin material. When a surface of a resin material has minute irregularities or the like which lower smoothness of the surface of the resin material, it is preferable to preliminarily make a surface shape of the resin material smooth by annealing treatment, surface polishing, formation of a coating film using a transparent coating material which forms a surface of a resin material into a smooth surface by being filled into irregularities formed on the surface of the resin material or the like. Further, it is also preferable to properly remove burrs and or like from the surface of resin material formed at the time of molding.

Water repellent treatment or oil repellent treatment may be applied to the surface of the resin functional portion 20. As the water repellent treatment or the oil repellent treatment, for example, fluororesin coating treatment, silicon-resin coating treatment or the like can be named. By applying the water repellent treatment or the oil repellent treatment to the surface of the resin functional portion 20, a fluid such as a body fluid is minimally adhered to the surface of the resin functional portion 20 during an operation. Accordingly, lowering of back-surface-side visibility through the resin functional portion 20 or lowering of light irradiation characteristic through the resin functional portion 20 can be suppressed as much as possible. Since the surface of the resin functional portion 20 is protected, it is also possible to acquire an advantageous effect that resistance to a drug solution can be enhanced, an advantageous effect that deterioration of the resin functional portion 20 can be prevented and the like. Although water repellent treatment or oil repellent treatment may be applied to the whole resin functional portion 20, water repellent treatment or oil repellent treatment may be applied in a limitative manner to the hook-shaped portion 40 which is a portion to which a body fluid or the like is liable to be adhered.

The trunk portion 30 has an approximately straight rod shape and extends toward a bent portion 60 formed between the trunk portion 30 and the hook-shaped portion 40 from a proximal end portion 30A of the trunk portion 30 which is fixed to the distal end of the grip portion 10. The trunk portion 30 functions as a support portion for supporting the hook-shaped portion 40 at a position away from the grip portion 10 by a fixed distance. The trunk portion 30 also has a function of a light guide passage which guides light incident on the trunk portion 30 from the proximal end portion 30A to the bent portion 60. Light which is emitted from the light source 12 accommodated in the grip portion 10 and is incident on the proximal end portion 30A is guided to the bent portion 60 through the inside of the trunk portion 30.

The trunk portion 30 is configured to irradiate a portion of light which passes through the inside of the trunk portion 30 to the periphery of the trunk portion 30 as leaked light, and an affected part which faces the back surface 34 of the trunk portion 30 is illuminated by the leaked light. Accordingly, when light passing through the inside of the trunk portion 30 is present in the trunk portion 30, compared to a case where there is no light passing through the inside of the trunk portion 30, back-surface-side visibility through the trunk portion 30 is enhanced.

The trunk portion 30 of the medical retractor 1 shown in FIG. 1 to FIG. 4 has a rectangular shape with rounded corners in cross section substantially perpendicular to a longitudinal direction of the trunk portion 30, and the front surface 31 and the back surface 34 form flat surfaces which are disposed parallel to each other. With such a configuration, light on the back surface side which has passed through the trunk portion 30 is transmitted to a front surface side through the trunk portion 30 with a low refraction quantity. Accordingly, back-surface-side visibility can be enhanced, and an affected part on a back surface side can be visually recognized in an actual size.

The hook-shaped portion 40 has a pointed shape where a width of the hook-shaped portion 40 is fixed and a thickness of the hook-shaped portion 40 is gradually decreased toward a distal end of the hook-shaped portion 40. A pointed end of the hook-shaped portion 40 has a rectangular shape with rounded corners. That is, thicknesses of respective portions of the hook-shaped portion 40 are adjusted corresponding to a retraction stress applied to the hook-shaped portion 40 at the time of using the medical retractor 1 for tissue retraction. Accordingly, a volume of a part of the hook-shaped portion 40 which has a possibility of entering a field of operation and becoming a shield during an operation can be decreased as much as possible while ensuring a strength of the medical retractor 1. Further, the hook-shaped portion 40 is made thinner toward a distal end thereof closest to an operation target part in the field of operation when a doctor makes an incision, suture or the like. Accordingly, the back-surface-side visibility of the hook-shaped portion 40 is also enhanced as the hook-shaped portion 40 approaches the operation target part.

Substantially the whole back surface 44 which is brought into contact with an affected part which is retracted by the hook-shaped portion 40 is formed into a flat surface and hence, a burden imposed on the affected part which is brought into contact with the hook-shaped portion 40 can be minimized. Further, a part between the back surface 44 and a right side surface 42 and a part between the back surface 44 and a left side surface 43 are respectively formed of a continuous curved surface having no corners and hence, there is no possibility that corner portions are brought into contact with the affected part whereby it is possible to further decrease a burden on the affected part with which the hook-shaped portion 40 is brought into contact.

The bent portion 60 maintains an angle of an approximately 90° between the extending direction of the trunk portion 30 and the extending direction of the hook-shaped portion 40. A radius of curvature R of the bent portion 60 can be variously changed, and can be set to a value which falls within a range of from 0 to 40 mm inclusive, for example. The smaller the radius of curvature R is, the more the ease of tissue retraction is enhanced. When the radius of curvature R is increased, strength and light guide efficiency of the bent portion 60 can be enhanced.

A distal end portion 45 of the hook-shaped portion 40 is bent inward so that the distal end portion 45 is formed into a pawl shape. With such a configuration, hook performance of the hook-shaped portion 40 at the time of retracting a tissue is enhanced.

With respect to an incident light from the proximal end portion 30A of the trunk portion 30, a portion of the incident light is irradiated to the outside of the resin functional portion 20 at the bent portion 60, and a remaining incident light is reflected on a surface of the bent portion 60 and advances toward the hook-shaped portion 40. Most of the light which advances inside of the hook-shaped portion 40 is irradiated from a portion in the vicinity of the distal end portion 45. That is, light is irradiated from the portion in the vicinity of the distal end portion 45 which is closest to the affected part and hence, visibility of the affected part is enhanced. As a matter of course, light is also irradiated from side surfaces of the front surface 41, the back surface 44 and the like of the hook-shaped portion 40 as leaked light and hence, it is possible to enhance the back-surface-side visibility where a tissue in the affected part hooked by the hook-shaped portion 40 is visually recognized from a front surface side.

As has been described heretofore, according to the medical retractor 1 of this embodiment, the resin functional portion 20 is made of a resin and hence, the resin functional portion 20 is light-weighted compared to a conventional steel-made retractor, and the degree of freedom in selecting a shape is also increased. Further, the resin functional portion 20 is not electrically conductive and hence, there is no possibility that a thermal burn is given to an affected part due to contact between an electrocautery or the like and the affected part. Since the resin functional portion 20 is made of a transparent resin, visibility of the affected part through the resin functional portion 20 is remarkably enhanced compared to the conventional steel-made retractor. In addition, light is made to pass through the resin functional portion 20 and hence, a field of operation is illuminated so that a field of view of the doctor is expanded and, further, the back-surface-side visibility is enhanced due to leaked light from the resin functional portion 20.

(2) Second Embodiment

Figure 5:
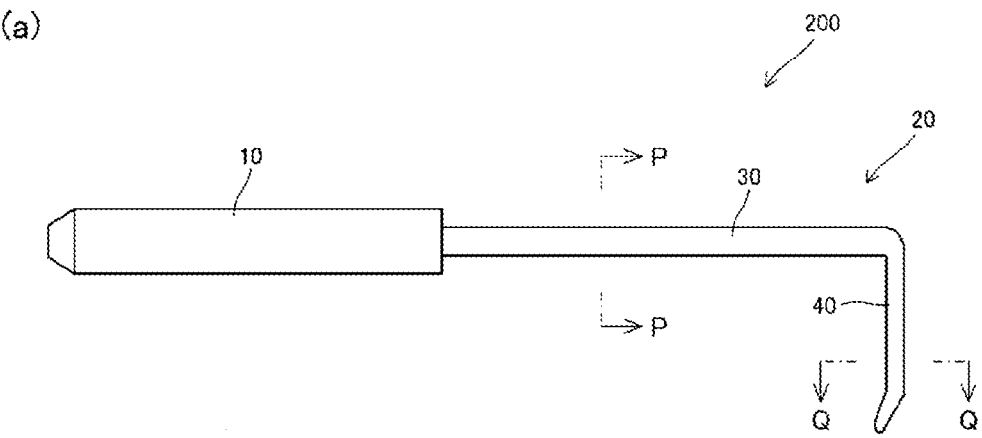
FIG. 5(a) to FIG. 5(c) are views for describing a shape of a medical retractor according to a second embodiment.
Figure 5:
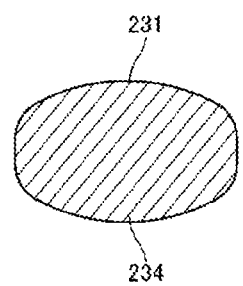
Figure 5:
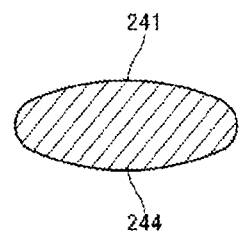

FIG. 5 is a view for describing a shape of a medical retractor 200 according to a second embodiment. The medical retractor 200 shown in FIG. 5 has substantially the same configuration as the medical retractor 1 according to the above-mentioned first embodiment except for shapes of a front surface and a back surface of a trunk portion 30 of a resin functional portion 20 and shapes of a front surface and a back surface of a hook-shaped portion 40 of the resin functional portion 20. Accordingly, the constitutional elements other than the back surface and the front surface of the resin functional portion 20 are given the same symbols as the corresponding constitutional elements of the first embodiment, and their detailed description is omitted.

The trunk portion 30 is formed into an approximately elliptical shape in cross section substantially perpendicular to the longitudinal direction of the trunk portion 30. Accordingly, front surfaces 231, 241 and back surfaces 234, 244 of the trunk portion 30 respectively have a convex-lens-like bulging shape.

In FIG. 5, both the front surfaces 231, 241 and the back surfaces 234, 244 are respectively formed into a convex-lens-like bulging shape. However, only one of the front surfaces 231, 241 and the back surfaces 234, 244 may be formed into a bulging shape. The back surface 244 of the hook-shaped portion 40 which is brought into contact with an affected part may be held in a flat surface shape for reducing a burden to a retracted affected part.

As described above, by forming at least one of the front surfaces 231, 241 and the back surfaces 234, 244 into a cylindrical lens shape having a mountain-like curved surface in cross section in a width direction, an affected part which faces the back surfaces 234, 244 can be visually recognized in an enlarged manner from the front surfaces 231, 241 side of the trunk portion 30. That is, the detail of the affected part can be visually recognized and hence, the back-surface-side visibility is enhanced.

A convex-lens-like bulging shape may be provided to the whole trunk portion 30 or may be provided only to a main part of the trunk portion 30. For example, the trunk portion 30 may be configured such that a convex-lens-like bulging shape is imparted to a main part of the trunk portion 30 on a back surface side where the visual recognition of an affected part in an enlarged manner is necessary, and a flat surface shape is imparted to other portions of the trunk portion 30 as in the case of the first embodiment. In this case, a convex-lens-like bulging shape imparted to the front surfaces 231, 241 and the back surfaces 234, 244 may be a spherical convex lens shape.

According to the medical retractor 200 of the above-mentioned second embodiment, a back surface side of the resin functional portion 20 can be visually recognized in an enlarged manner by imparting the convex-lens-like bulging shape to at least one of the front surfaces 231, 241 and the back surfaces 234, 244. Accordingly, the back-surface-side visibility can be further enhanced. Further, the rigidity of the resin functional portion 20 is enhanced by imparting a bulging shape to the trunk portion 30 and hence, durability of the medical retractor 200 is also enhanced.

(3) Third Embodiment

Figure 6:
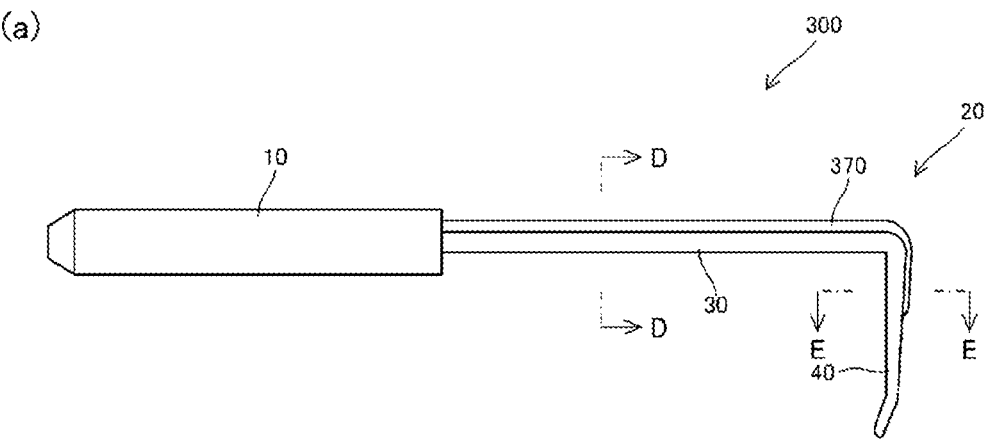
FIG. 6(a) to FIG. 6(c) are views for describing a shape of a medical retractor according to a third embodiment.
Figure 6:
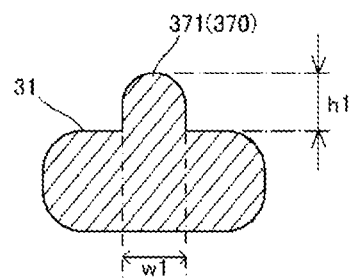
Figure 6:
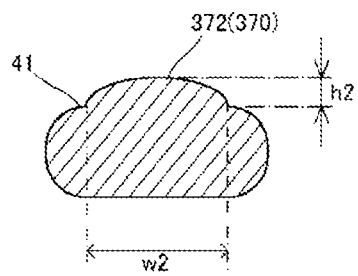

FIG. 6 is a view for describing a shape of a medical retractor 300 according to a third embodiment. The medical retractor 300 shown in FIG. 6 has substantially the same configuration as the medical retractor 1 according to the above-mentioned first embodiment except for a point that a ridge is formed on front surfaces 31, 41 of a resin functional portion 20. Accordingly, the constitutional elements other than the ridge are given the same symbols as the corresponding constitutional elements of the first embodiment, and their detailed description is omitted.

In the medical retractor 300, a ridge 370 is formed on the front surfaces 31, 41 of the resin functional portion 20 in an extending manner along the longitudinal direction of the resin functional portion 20 at substantially center of the front surfaces 31, 41. By forming the ridge 370 on the resin functional portion 20, the resin functional portion 20 is reinforced so that rigidity of the resin functional portion 20 against a stress applied to the resin functional portion 20 is enhanced. With such a configuration, the medical retractor 300 can surely acquire rigidity sufficient for tissue retraction while realizing the reduction of weight compared to a conventional steel-made retractor.

As shown in FIG. 6(b) and FIG. 6(c), in the ridge 370, a first portion 371 which is formed from the front surface 31 of the trunk portion 30 to the front surface of a bent portion 60 and a projecting shape of a second portion 372 which is formed on the front surface of the bent portion 60 and the front surface 41 of a hook-shaped portion 40 may have different projecting shapes.

To be more specific, as shown in FIG. 6(b), the first portion 371 of the ridge 370 is formed so as to have a bell-shaped cross section where a projection height is large and a width is small. On the other hand, as shown in FIG. 6(C), the second portion 372 of the ridge 370 is formed of an arcuate raised ridge having a small projection height and a large width. That is, the first portion 371 is set higher than the second portion 372 in height (h1>h2), and the first portion 371 is set narrower than the second portion 372 in width (w1<w2).

It is preferable to form a connecting portion where a height and a width of the ridge 370 gradually change between the first portion 371 and the second portion 372. In FIG. 6(c), although stepped portions are provided between the second portion 372 and the front surface 41, the second portion 372 may be configured to be smoothly and continuously connected to the right side surface 42 and the left side surface 43.

As described above, by changing a shape of the ridge 370 between the first portion 371 formed from the front surface 31 of the trunk portion 30 to the bent portion 60 and the second portion 372 formed from the bent portion 60 to the hook-shaped portion 40, it is possible to improve also back-surface-side visibility of the medical retractor 300 while enhancing rigidity in a portion ranging from the trunk portion 30 to the bent portion 60 where a stress load is large and while enhancing visibility of a field of operation by reducing a thickness in a hook-shaped portion 40 close to an operation target part. It is needless to say that the whole ridge 370 may be formed to have a bell-shaped cross section where a projection height is large and a width is narrow as in the case of the first portion 371, or the whole ridge 370 may be formed of an arcuate raised ridge where a projection height is small and a width is large as in the case of the second portion 372.

(4) Fourth Embodiment

Figure 7:
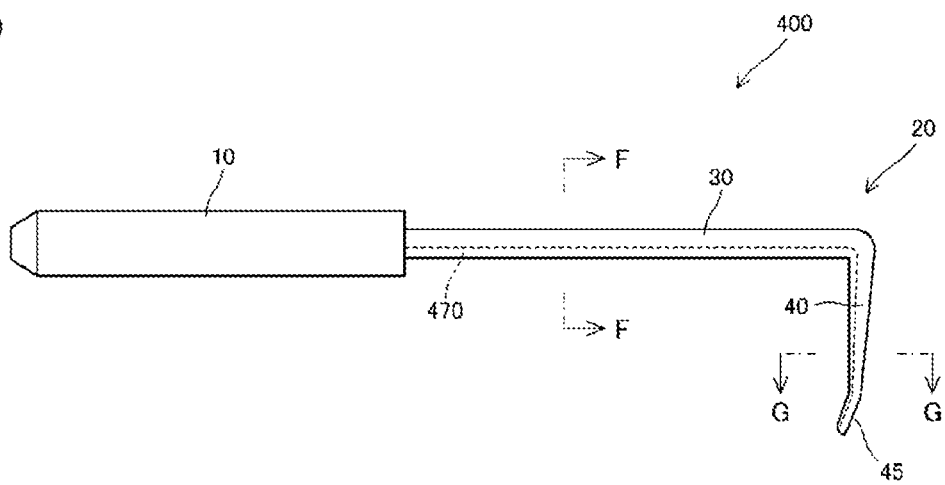
FIG. 7(a) to FIG. 7(c) are views for describing a shape of a medical retractor according to a fourth embodiment.
Figure 7:
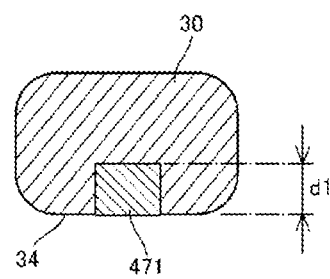
Figure 7:
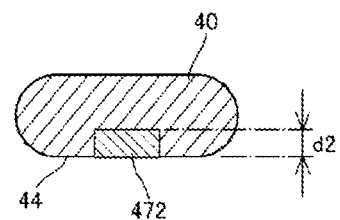

FIG. 7 is a view for describing a shape of a medical retractor 400 according to a fourth embodiment. The medical retractor 400 shown in FIG. 7 has substantially the same configuration as the medical retractor 1 according to the above-mentioned first embodiment except for a point that a light guiding portion is formed on back surfaces 33, 34 of a resin functional portion 20. Accordingly, the constitutional elements other than the light guiding portion are given the same symbols as the corresponding constitutional elements of the first embodiment, and their detailed description is omitted.

In the medical retractor 400, a light guiding portion 470 which extends to the distal end portion 45 or to a portion in the vicinity of the distal end portion 45 of a hook-shaped portion 40 is formed on the back surfaces 34, 34 of the resin functional portion 20 along the longitudinal direction at substantially center of the back surfaces 34, 34. The light guiding portion 470 can be formed by embedding a resin material having a property different from a property of a resin material for forming the resin functional portion 20 in the back surfaces 33, 34 of the resin functional portion 20.

The light guiding portion 470 is made of a material having transparency and refractivity different from those of a material for forming the body of the resin functional portion 20. For example, by forming the light guiding portion 470 using a resin material having higher transparency than a resin material for forming the resin functional portion 20, light guide efficiency in guiding light incident on the resin functional portion 20 from a proximal end of the resin functional portion 20 to a distal end of the resin functional portion 20 is enhanced.

As shown in FIG. 7(b) and FIG. 7(c), a thickness of the light guiding portion 470 may differ between a first portion 471 formed from the back surface 34 of the trunk portion 30 to the front surface of the bent portion 60 and a second portion 472 formed on the back surface of the bent portion 60 and on the back surface 44 of the hook-shaped portion 40.

To be more specific, a thickness d2 of the second portion 472 shown in FIG. 7(c) is set relatively small compared to a thickness d1 of the first portion 471 shown in FIG. 7(b). In the second portion 472, the thickness of the second portion 472 may be adjusted corresponding to the thickness of the hook-shaped portion 40.

In this manner, by changing the thickness of the light guiding portion 470 between the first portion 471 formed from the back surface 34 of the trunk portion 30 to the front surface of the bent portion 60 and the second portion 472 formed from the bent portion 60 to the hook-shaped portion 40, the light guiding portion 470 can be formed with a suitable thickness corresponding to a thickness of the resin functional portion 20.

(5) Fifth Embodiment

Figure 8:
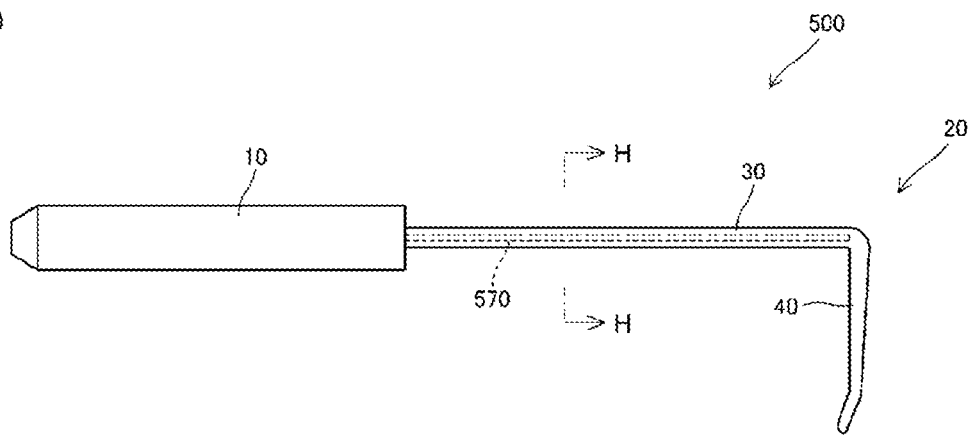
FIG. 8(a) to FIG. 8(c) are views for describing a shape of a medical retractor according to a fifth embodiment.
Figure 8:
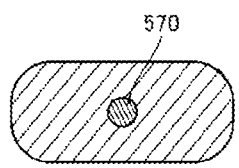
Figure 8:
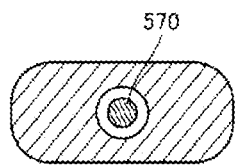

FIG. 8 is a view for describing a shape of a medical retractor 500 according to a fifth embodiment. The medical retractor 500 shown in FIG. 8 has substantially the same configuration as the medical retractor 1 according to the above-mentioned first embodiment except for a point that a light guiding portion is formed in the inside of a resin functional portion 20. Accordingly, the constitutional elements other than the light guiding portion are given the same symbols as the corresponding constitutional elements of the first embodiment, and their detailed description is omitted.

In the medical retractor 500, a light guiding portion 570 which extends in the inside of the resin functional portion 20 along a longitudinal direction is formed. With such a configuration, light guide efficiency in guiding light incident on the resin functional portion 20 from a proximal end of the resin functional portion 20 to a distal end of the resin functional portion 20 is enhanced.

As shown in FIG. 8(b), the light guiding portion 570 can be formed by embedding a light guide member such as an optical fiber by insert molding where a resin is injected into a die in a state where the light guide member is inserted into the die. Alternatively, the light guiding portion 570 can be formed by two-color molding. Further, as shown in FIG. 8(c), the light guiding portion 570 may be formed by inserting a light guide member such as an optical fiber into an insertion hole formed in the resin functional portion 20 along the longitudinal direction of the resin functional portion 20 from the proximal end of the resin functional portion 20.

FIG. 8 shows the case where the light guiding portion 570 is formed only in the trunk portion 30. However, the light guiding portion 570 may be extended to a hook-shaped portion 40 or may be exposed to the outside at an intermediate portion of the hook-shaped portion 40 such that an affected part is illuminated by light irradiated from the light guiding portion 570.

(6) Sixth Embodiment

Figure 9:
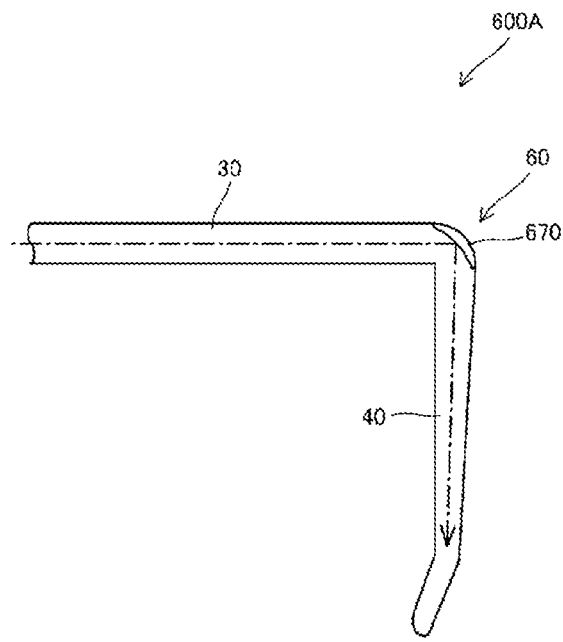
FIG. 9 is a view for describing a shape of a medical retractor according to a sixth embodiment.
Figure 10:
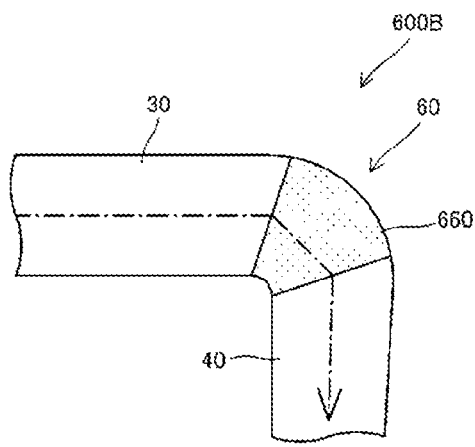
FIG. 10 is a view for describing a shape of a medical retractor according to the sixth embodiment.

FIG. 9 is a view for describing a shape of a medical retractor 600A according to a sixth embodiment. FIG. 10 is a view for describing a shape of a medical retractor 600B according to the sixth embodiment. The medical retractors 600A, 600B shown in these drawings respectively have substantially the same configuration as the medical retractor 1 according to the above-mentioned first embodiment except for a point that a light guiding structure for guiding light toward a hook-shaped portion 40 is provided to a bent portion 60. Accordingly, the constitutional elements other than the light guiding structure of the bent portion 60 are given the same symbols as the corresponding constitutional elements of the first embodiment, and their detailed description is omitted.

In the medical retractor 600A shown in FIG. 9, a light reflecting portion 670 is provided to the bent portion 60. The light reflecting portion 670 reflects light which advances inside of a trunk portion 30 to a distal end from a proximal end of the trunk portion 30 toward a distal end of the hook-shaped portion 40 at the bent portion 60.

The light reflecting portion 670 can be formed by providing a light reflection structure, or by adhering or embedding a light reflecting material to or in the bent portion 60 along a surface, particularly, an outer peripheral surface of the bent portion 60. A light reflecting material can be embedded by insert molding in such a manner that a resin is injected into a die in a state where the light reflecting material is inserted into the die, for example.

The medical retractor 600B shown in FIG. 10 has a prism structure 660 on the bent portion 60. The prism structure 660 makes light which advances in the inside of the trunk portion 30 from the proximal end to the distal end of the trunk portion 30 deflect and advance toward the distal end of the hook-shaped portion 40.

The light reflecting portion 670 can be formed by embedding a prism member in the inside of the bent portion 60. The prism member can be embedded by insert molding in such a manner that a resin is injected into a die in a state where the prism member is inserted into the die, for example.

By providing the light reflecting portion 670 or the prism structure 660 as described above, an irradiation amount of light from the distal end or the like of the hook-shaped portion 40 is increased and hence, illumination performance of an affected part of the medical retractor is enhanced. Further, an amount of leaked light from the hook-shaped portion 40 is also increased and hence, back-surface-side visibility is enhanced.

(7) Seventh Embodiment

Figure 26:
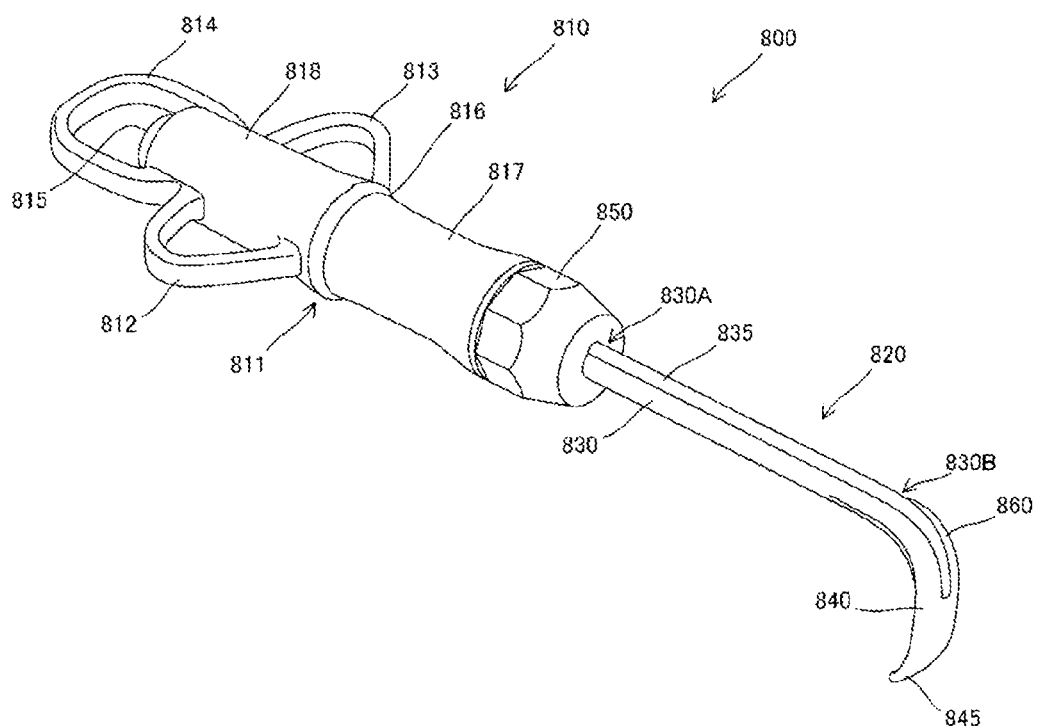
FIG. 26 is a perspective view of a medical retractor according to a seventh embodiment.
Figure 27:
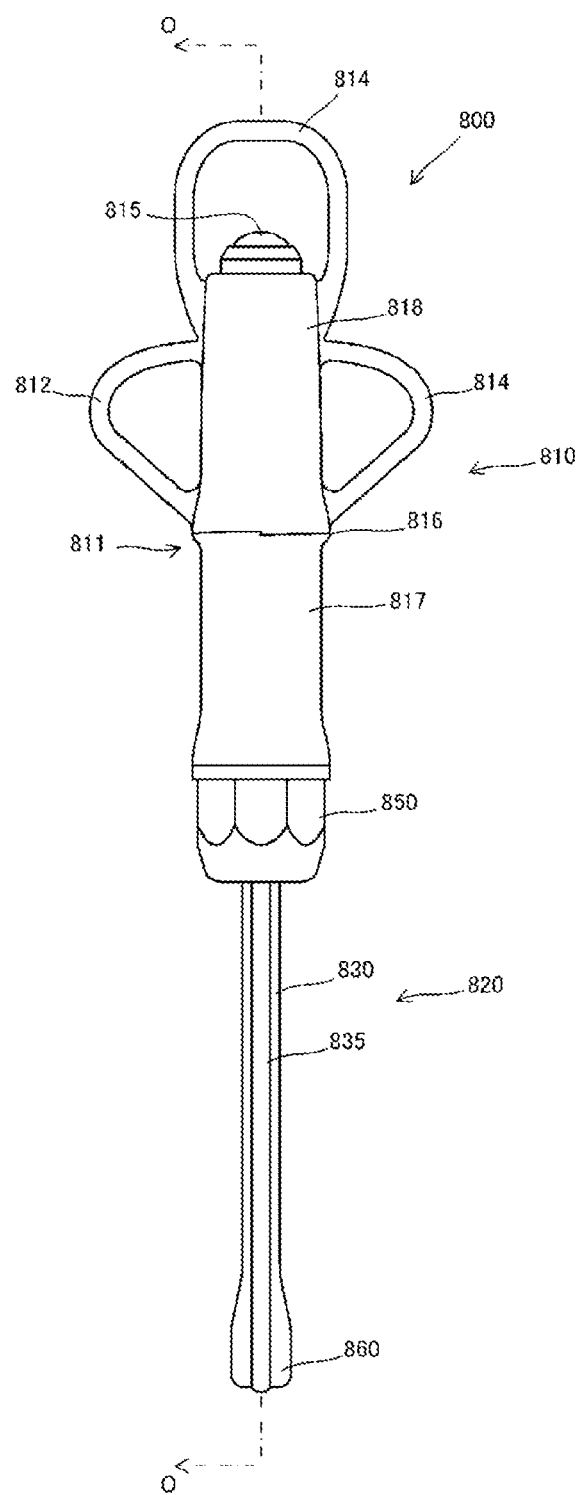
FIG. 27 is a plan view of the medical retractor according to the seventh embodiment.
Figure 28:
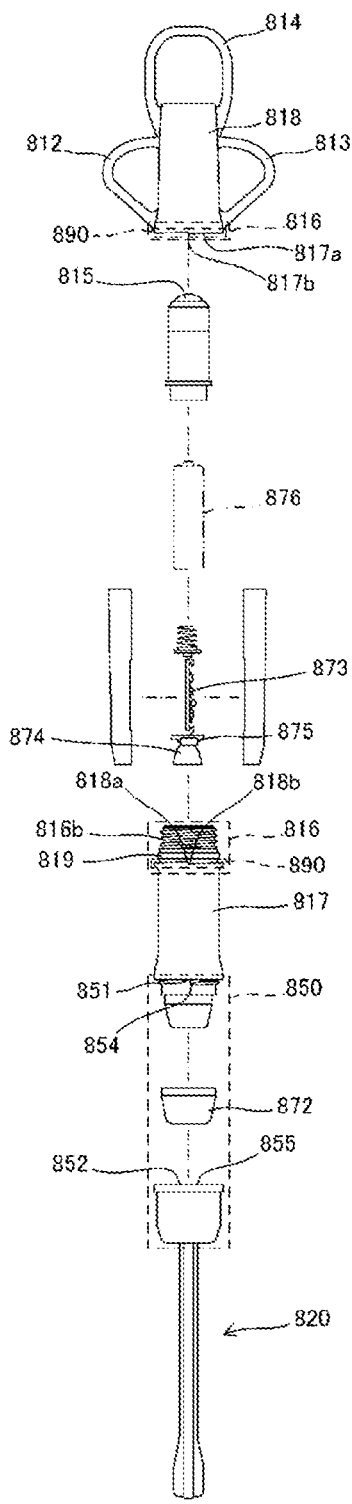
FIG. 28 is an exploded view of the medical retractor according to the seventh embodiment.
Figure 29:
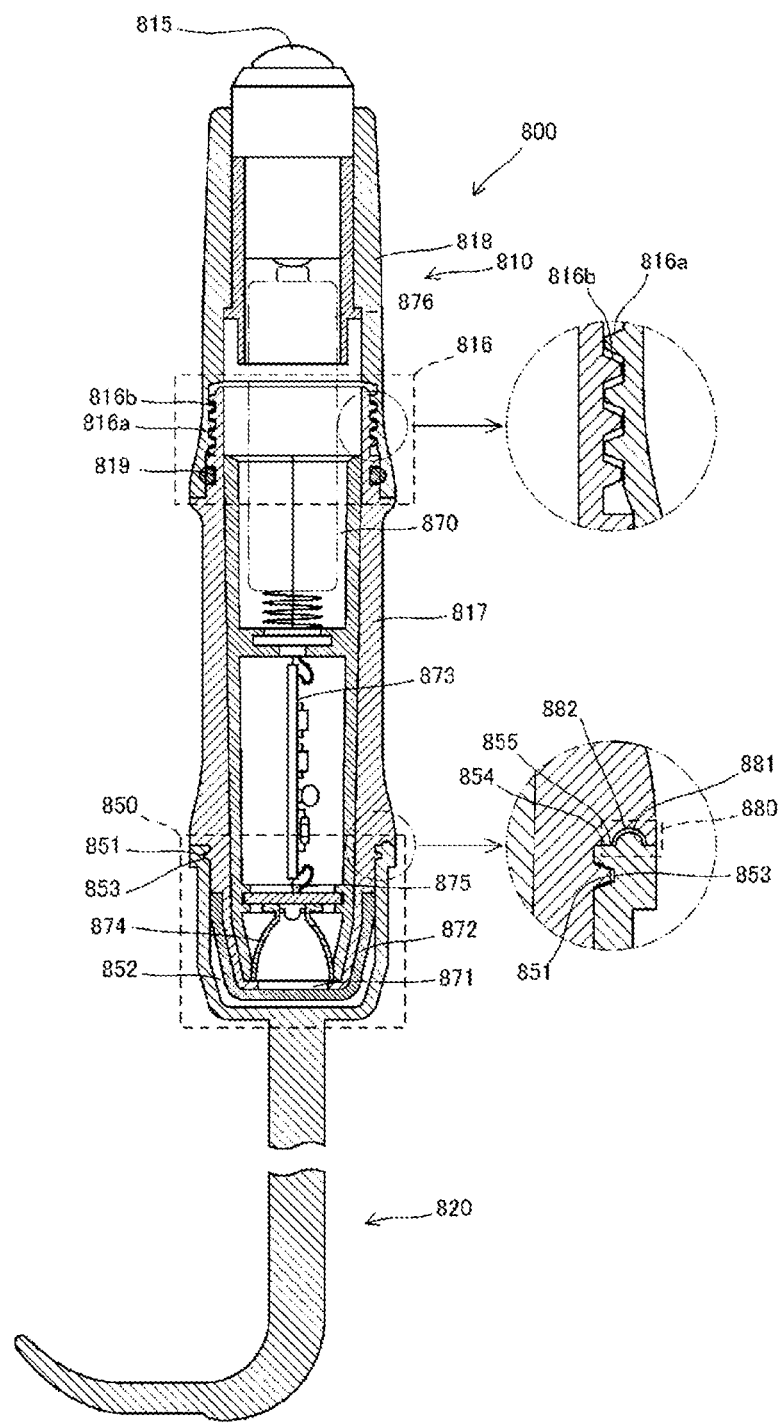
FIG. 29 is a cross-sectional view of the medical retractor according to the seventh embodiment.
Figure 30:
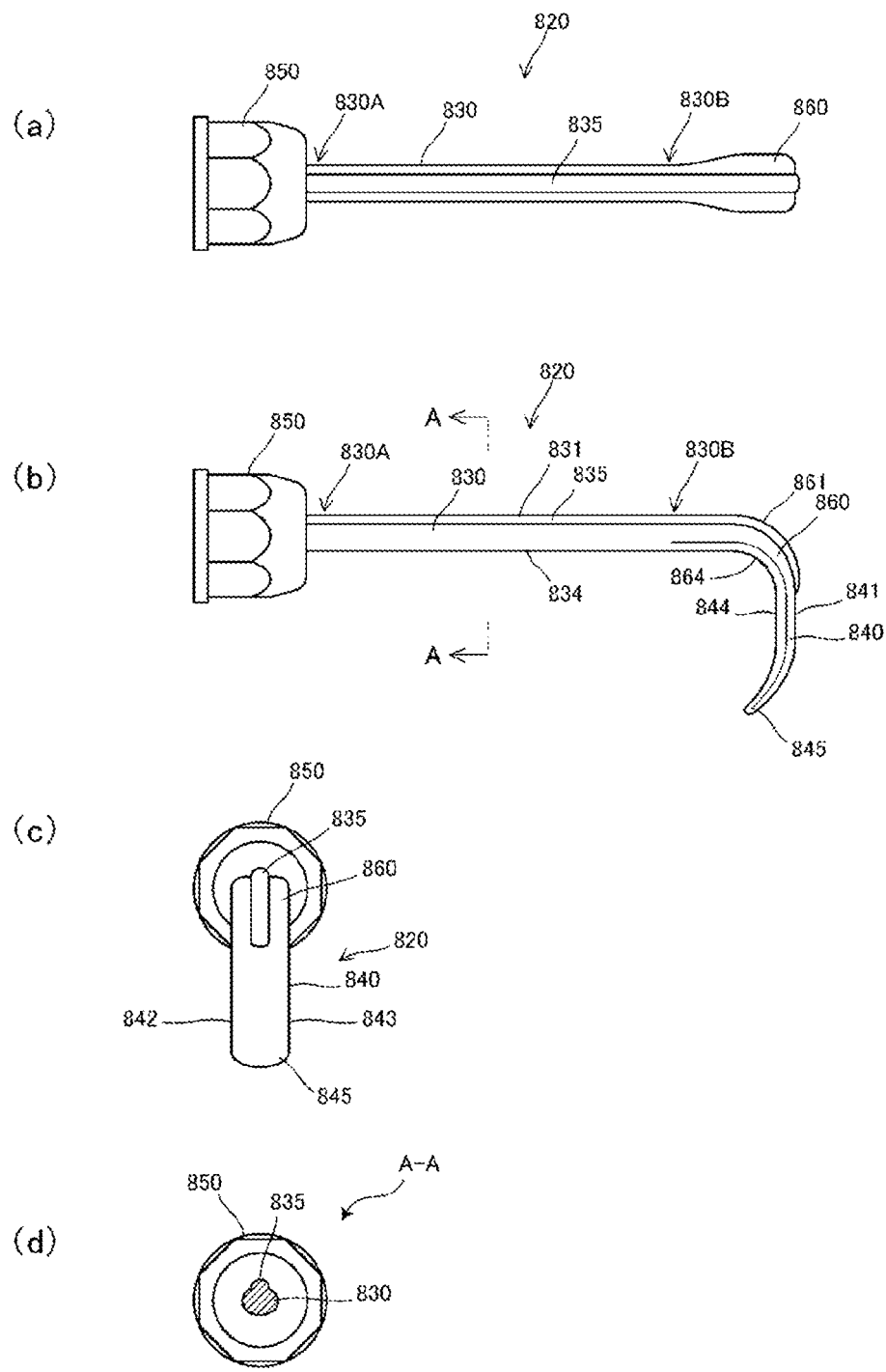
FIG. 30(a) to FIG. 30(d) are views of a functional resin portion of the medical retractor according to the seventh embodiment as viewed from respective surfaces.

FIG. 26 to FIG. 30(*d*) are views for describing a medical retractor 800 according to a seventh embodiment. FIG. 26 is a perspective view of the medical retractor 800, FIG. 27 is a plan view of the medical retractor 800, FIG. 28 is an exploded view of the medical retractor 800, FIG. 29 is a cross-sectional view of the medical retractor 800, and FIG. 30(*a*) to FIG. 30(*d*) are views of a resin functional portion of the medical retractor 800 as viewed from respective sides.

Schematically, the medical retractor 800 has substantially the same configuration as the medical retractor 1 according to the first embodiment, and includes a grip portion 810 which a practitioner such as a doctor or an assistant holds, and a resin functional portion 820 which is used by being connected and fixed to a distal end of the grip portion 810.

A grip portion 810 has an accommodating space 870 in which an LED which forms a light source 875 and a battery which forms a power source 876 for the LED are accommodated in a fixed state. The light source 875 is fixed in the inside of the accommodating space 870 with a light emitting surface thereof directed to a distal end side of the grip portion 810 (a proximal end of the resin functional portion 820). As a battery which forms the power source 876, in this embodiment, an elongated circular columnar shaped AA-sized battery is adopted. Although a material for forming the grip portion 810 and a shape of the grip portion 810 are not particularly limited, the grip portion 810 can be manufactured using a lightweight resin or lightweight metal. The grip portion 810 has an outer surface shape which allows a user to acquire favorable grip performance when the user holds the grip portion 10.

The grip portion 810 includes a barrel portion 811, a right finger hook portion 812, a left finger hook portion 813, a rear finger hook portion 814, and a switch 815 in external appearance. The barrel portion 811 is formed by connecting a distal end side barrel portion 817 and a tail end side barrel portion 818 to each other by way of the connecting portion 816. The right finger hook portion 812, the left finger hook portion 813 and the rear finger hook portion 814 are mounted on the tail end side barrel portion 818.

When the switch 815 is operated, an ON state or an OFF state of the power supply from the power source 876 to the light source 875 accommodated in the accommodating space 870 is changed over. Accordingly, an ON state or an OFF state of light irradiated from the light source 875 toward the resin functional portion 820 can be changed over. An operation using the switch 815 is not limited to turning ON and OFF of the power supply, and a power source supply amount adjusting operation during an ON state (a light irradiation amount adjusting operation of the light source 875) may be performed using the switch 815.

The barrel portion 811 is formed as an integral body by threadedly connecting a male threaded structure 816*b* which is formed on an outer peripheral surface of the other end portion to a female threaded structure 816*a* which is formed on an inner peripheral surface of one end portion at the connecting portion 816 between the distal end side barrel portion 817 and the tail end side barrel portion 818.

With respect to threads of the female threaded structure 816*a* and the male threaded structure 816*b*, a crest portion of each thread is cut and hence, the thread has a truncated conical shape in cross section. Accordingly, a worn-out speed of the crest portion attributed to a thread rotating operation is alleviated thus prolonging a durable lifetime of the female threaded structure 816*a* and the male threaded structure 816*b* compared to a case where threads whose crest portion is not cut are adopted.

In a state where the distal end side barrel portion 817 and the tail end side barrel portion 818 are integrally connected to each other, a groove 819 in which an O ring is fitted is formed respectively on portions of the distal end side barrel portion 817 and the tail end side barrel portion 818 in an extending manner in the circumferential direction of the barrel portion 811 such that the grooves 819 opposedly face each other. With such a configuration, it is possible to prevent the intrusion of blood, a body fluid, various kinds of moistures used during an operation and the like into the inside of the accommodating space 870 through a gap formed in the connecting portion 816. FIG. 28 and FIG. 29 respectively show a state where the O ring is fitted in the groove 819.

At the connecting portion 816, a rotation amount regulation means 890 which regulates a threaded rotation amount between the distal end side barrel portion 817 and the tail end side barrel portion 818 in a fastening direction such that a threaded rotation amount does not exceed a predetermined amount is disposed. The rotation amount regulation means 890 also has a function of positioning the fastening rotation at the time of integrating the distal end side barrel portion 817 and the tail end side barrel portion 818 to each other by threaded engagement.

In examples shown in FIG. 27 to FIG. 29, the rotation amount regulation means 890 is formed of stepped portions 817*b*, 818*b* which are formed on an end surface 817*a* of the distal end side barrel portion 817 and an end surface 818*a* of the tail end side barrel portion 818 respectively in a state where the end surfaces 817*a*, 818*a* are brought into contact with each other in an opposedly facing manner when the distal end side barrel portion 817 and the tail end side barrel portion 818 are formed into an integrated body by threaded connection. Stepped surfaces of the stepped portions 817*b*, 818*b* formed on these end surfaces 817*a*, 818*a* are respectively directed in the fastening direction of the threaded rotation. When a threaded rotation amount between the distal end side barrel portion 817 and the tail end side barrel portion 818 reaches a predetermined amount, the stepped surfaces of the stepped portions 817*b*, 818*b* impinge each other and are brought into contact with each other in an opposedly facing manner so that further advancing of the threaded rotation in the fastening direction is regulated.

A distal end of the grip portion 810 and a tail end of the resin functional portion 820 are connected and fixed to each other by a connecting portion 850 so that the grip portion 810 and the resin functional portion 820 are formed into an integral body. By releasing the connection and removing the resin functional portion 820, it is possible to exchange the resin functional portion 820 by connecting a different resin functional portion 820 to the grip portion 810.

A male thread structure 851 is formed on an outer peripheral surface of a distal end portion of the grip portion 810. The resin functional portion 820 has a recessed portion 852 indented toward a distal end of the resin functional portion 820 on a proximal end portion thereof, and a female thread structure 853 is provided to an inner peripheral surface of the recessed portion 852. The recessed portion 852 of the resin functional portion 820 has a size suitable for fitting engagement with the distal end of the grip portion 810. By inserting the distal end of the grip portion 810 into the recessed portion 852 and by making the female thread structure 853 and the male thread structure 851 threadedly engage with each other, the grip portion 810 and the resin functional portion 820 can be connected to each other as an integral body.

In the connecting portion 850, an antislip structure for preventing slippage of the grip portion 810 and the resin functional portion 820 at the time of rotating the grip portion 810 and the resin functional portion 820 in a fastening direction or in a loosening direction is provided to an outer surface of a proximal end of the resin functional portion 820 which covers the distal end of the grip portion 810 from the outside. In an example shown in FIG. 26, an outer surface of the proximal end of the resin functional portion 820 is formed in an approximately octagonal shape in cross section in the longitudinal direction of the medical retractor 800. With such a configuration, gripping ease at the time of applying a force in the fastening direction or in the loosening direction to the proximal end of the resin functional portion 820 can be enhanced.

A distal end surface of the grip portion 810 is made of a transparent resin so that the inside of the accommodating space 870 can be viewed in a see-through manner. To be more specific, a hole 871 which communicates with the accommodating space 870 is formed in the distal end of the resin-made distal end side barrel portion 817 of the grip portion 810, and a cap-shaped part 872 made of a transparent resin which covers the hole 871 is adhered to the distal end side barrel portion 817 so as to cover the distal end of the distal end side barrel portion 817 with no gap thus sealing the hole 871. With such a configuration, the intrusion of blood, a body fluid, various kinds of moistures used during an operation or the like into the inside of the accommodating space 870 can be prevented while allowing light emitted from the light source 875 to be irradiated from the distal end of the grip portion 810.

A portion of the cap-shaped part 872 which covers the hole 871 is formed of a flat surface. With such a configuration, light which the light source 875 in the inside of the accommodating space 870 irradiates passes through the cap-shaped part 872 with a low loss. The LED which forms the light source 875 is fixed to an area in the vicinity of the distal end of a printed circuit board 873 disposed in the inside of the accommodating space 870, and a space defined between a light emitting part of the LED and the hole 871 is surrounded by a cylindrical reflector 874 for converging light, and the reflector 874 has a shape where a diameter of the reflector 874 in the vicinity of the hole 871 is larger than a diameter of the reflector 874 in the vicinity of the light source 875, and a diameter of the reflector 874 is gradually increased as the reflector 874 approaches the hole 871 from the light source 875. By providing the reflector 874, light of the light source 875 is efficiently irradiated to the resin functional portion 820 from the distal end of the grip portion 810.

At the connecting portion 850, a rotation amount regulation means 880 which regulates a threaded rotation amount in a fastening direction between the distal end side barrel portion 817 and the tail end side barrel portion 818 such that a threaded rotation amount does not exceed a predetermined amount is disposed. The rotation amount regulation means 880 functions as a member for positioning the fastening rotation at the time of integrating the distal end side barrel portion 817 and the resin functional portion 820 to each other by threaded engagement.

In an example shown in FIG. 29, the rotation amount regulation means 880 is formed of an engaging projection 881 and an engaging recessed portion 882 which are respectively formed on an end surface 854 of the distal end side barrel portion 817 and an end surface 855 of the resin functional portion 820 which are brought into contact with each other in an oppositely facing manner when the male thread structure 851 provided to the distal end portion of the grip portion 810 is threadedly connected to the female thread structure 853 of the recessed portion 852 in the connecting portion 850 so that the grip portion 850 and the resin functional portion 820 are formed as an integral body. When a threaded rotation amount between the distal end side barrel portion 817 and the resin functional portion 820 reaches a predetermined amount so that the end surfaces 854, 855 are brought into contact with each other, the engaging projection 881 and the engaging recessed portion 882 respectively formed on these end surfaces 854, 855 are engaged with each other by concavo-convex fitting while generating click feeling thus regulating further advancing of the threaded rotation in the fastening direction.

The resin functional portion 820 includes: a trunk portion 830 which has a proximal end portion 830A thereof connected and fixed to the grip portion 810; and a hook-shaped portion 840 which extends from a distal end portion 830B of the trunk portion 830 in a state where the hook-shaped portion 840 is bent in a hook shape through a bent portion 860. The trunk portion 830 is formed such that an affected part which faces back surfaces 834, 844, 864 of the trunk portion 830 can be viewed from front surface 831, 841, 861 sides of the trunk portion 830 in a see-through manner. A material for forming the resin functional portion 820, a surface treatment applied to the resin functional portion 820 and the like are substantially equal to those adopted by the medical retractor 1 according to the first embodiment and hence, their detailed description is omitted hereinafter.

The trunk portion 830 has an approximately straight rod shape and extends toward a bent portion 860 formed between the trunk portion 830 and the hook-shaped portion 840 from a proximal end portion 830A of the trunk portion 830 which is fixed to the distal end of the grip portion 810. The trunk portion 830 functions as a support portion for supporting the hook-shaped portion 840 at a position away from the grip portion 10 by a fixed distance. The trunk portion 830 also has a function of a light guide passage which guides light incident on the trunk portion 830 from the proximal end portion 830A to the bent portion 860. Light which is emitted from the light source 875 accommodated in the grip portion 810 and is incident on the proximal end portion 830A is guided to the bent portion 860 through the inside of the trunk portion 830.

The trunk portion 830 is configured to irradiate a portion of light which passes through the inside of the trunk portion 830 to the periphery of the trunk portion 830 as leaked light, and an affected part which opposedly faces the back surface 834 of the trunk portion 830 is illuminated by the leaked light. Accordingly, when light passing through the inside of the trunk portion 830 is present in the trunk portion 830, compared to a case where there is no light passing through the inside of the trunk portion 830, back-surface-side visibility through the trunk portion 830 is enhanced.

The trunk portion 830 of the medical retractor 800 has an elliptical shape in cross section substantially perpendicular to a longitudinal direction of the trunk portion 830, and a ridge 835 is formed on the front surfaces 831, 841 of the trunk portion 830 in an extending manner along the longitudinal direction of the trunk portion 830 at the substantially center of the front surfaces 831, 841. By forming a cross-sectional shape of the trunk portion 830 into an elliptical shape near a circular shape, a light guide efficiency in guiding light which is incident on the resin functional portion 820 from a proximal end of the resin functional portion 820 to a distal end portion of the resin functional portion 820 is enhanced. By providing the ridge 835 on the front surfaces 831, 841, the resin functional portion 820 is reinforced so that rigidity of the resin functional portion 820 against a stress applied to the resin functional portion 820 is increased.

The bent portion 860 is formed at a non-right angle where both an inner periphery which the back surface 864 forms and an outer periphery which the front surface 861 forms have a predetermined roundness. With such a configuration, a stress is minimally concentrated on a portion of the bent portion 860 where the trunk portion 830 and the hook-shaped portion 840 are connected to each other. Further, a stress which is applied to the resin functional portion 820 when a retraction stress is applied to the medical retractor 800 is received by the whole resin functional portion 820 in a dispersed manner thus realizing a shape by which a crack, breaking or the like minimally occurs in the medical retractor 800.

The resin functional portion 820 is gradually widened or flattened in the vicinity of a boundary between the trunk portion 830 and the bent portion 860, and is continuously connected to the hook-shaped portion 840 having a widened and flattened shape.

Substantially the whole back surface 844 which is brought into contact with an affected part which is retracted by the hook-shaped portion 840 is formed into an approximately flat surface with slight roundness and hence, a burden imposed on the affected part which is brought into contact with the hook-shaped portion 840 can be minimized. Further, a part between the back surface 844 and a right side surface 842 and a part between the back surface 844 and a left side surface 843 are respectively formed of a continuous curved surface having no corners and hence, there is no possibility that corner portions are brought into contact with the affected part whereby it is possible to further decrease a burden on the affected part with which the hook-shaped portion 840 is brought into contact.

The bent portion 860 maintains an angle between the extending direction of the trunk portion 830 and the extending direction of the hook-shaped portion 840 at an angle slightly inclined inward with respect to an approximately 90°. A distal end portion 845 of the hook-shaped portion 840 is bent inward so that the distal end portion 845 is formed into a pawl shape. With such a configuration, hook performance of the hook-shaped portion 840 at the time of retracting a tissue is enhanced.

With respect to an incident light from the proximal end portion 830A of the trunk portion 830, a portion of the incident light is irradiated to the outside of the resin functional portion 820 at the bent portion 860, and a remaining incident light is reflected on a surface of the bent portion 860 and advances toward the hook-shaped portion 840. Most of the light which advances in the inside of the hook-shaped portion 840 is irradiated from a portion in the vicinity of the distal end portion 845. That is, light is irradiated from the portion in the vicinity of the distal end portion 845 which is closest to the affected part and hence, visibility of the affected part is enhanced. As a matter of course, light is also irradiated from side surfaces of the front surface 841, the back surface 844 and the like of the hook-shaped portion 840 as leaked light and hence, it is possible to enhance the back-surface-side visibility where a tissue in the affected part hooked by the hook-shaped portion 840 is visually recognized from a front surface side.

As has been described heretofore, according to the medical retractor 800 of this embodiment, the resin functional portion 20 is made of a resin and hence, the resin functional portion 20 is light-weighted compared to a conventional steel-made retractor, and the degree of freedom in selecting a shape is also increased. Further, the resin functional portion 20 is not electrically conductive and hence, there is no possibility that a thermal burn is given to an affected part due to contact between an electrocautery or the like and the affected part. Since the resin functional portion 20 is made of a transparent resin, visibility of the affected part through the resin functional portion 20 is remarkably enhanced compared to the conventional steel-made retractor. In addition, light is made to pass through the resin functional portion 20 and hence, a field of operation is illuminated so that a field of view of the doctor is expanded and, further, the back-surface-side visibility is enhanced due to leaked light from the resin functional portion 20.

(8) Eighth Embodiment

Figure 31:
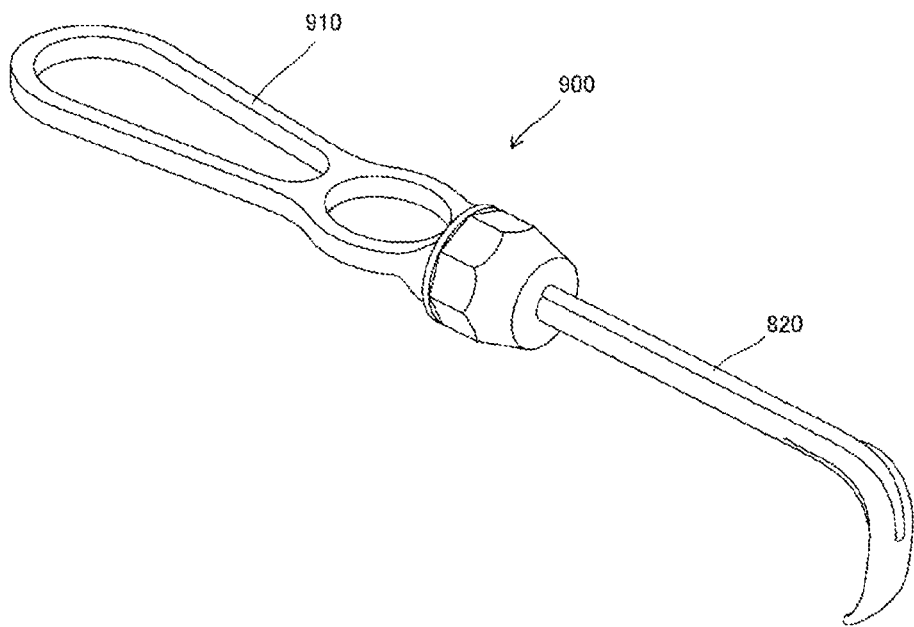
FIG. 31 is a view for describing a medical retractor according to an eighth embodiment.

FIG. 31 is a view for describing a medical retractor 900 according to the eighth embodiment. The medical retractor 900 has substantially the same configuration as the medical retractor 800 according to the above-mentioned seventh embodiment with respect to a resin functional portion and hence, the detailed description of the configuration of the resin functional portion of the medical retractor 900 is omitted hereinafter.

The grip portion 910 of the medical retractor 900 has substantially the same shape as a shape of a grip portion of a conventional metal-made medical retractor. To a distal end of the grip portion 910, a male threaded structure which is substantially equal to the male threaded structure provided to the distal end of the grip portion 810 of the above-mentioned seventh embodiment is provided. By connecting the resin functional portion 820 of the above-mentioned seventh embodiment to the distal end of the grip portion 910 thus forming the grip portion 910 and the resin functional portion 820 into an integral body, it is possible to realize a resin-made medical retractor which is substantially equal to a conventional metal-made medical retractor as a whole. In this manner, the medical retractor 900 according to this embodiment can be used by suitably replacing the medical retractor 800 according to the above-mentioned seventh embodiment with a resin-made retractor which can give substantially the same feeling of use as the conventional metal-made medical retractor to a user.

(9) Other Modifications

Besides the above-mentioned embodiments, the medical retractor 1, 200, 300, 400, 500, 600A, 600B, and 800 can be variously modified, and some of such modifications are described hereinafter.

FIG. 11 to FIG. 16 are views showing various modifications of the shape of the hook-shaped portion.

Figure 11:
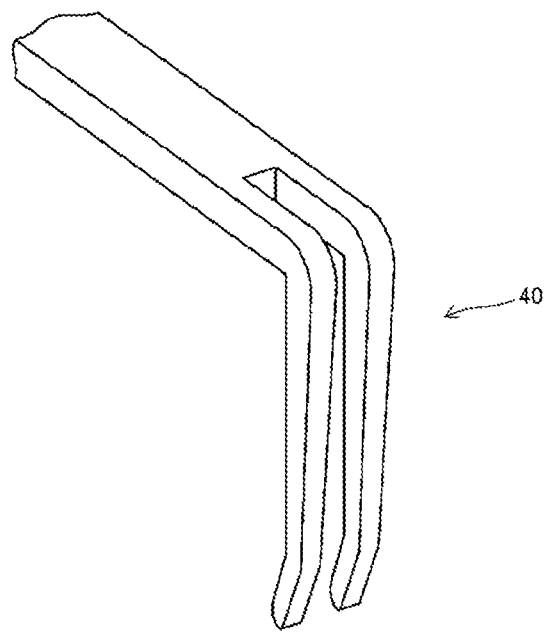
FIG. 11 is a view showing a modification of the shape of the hook-shaped portion.
Figure 12:
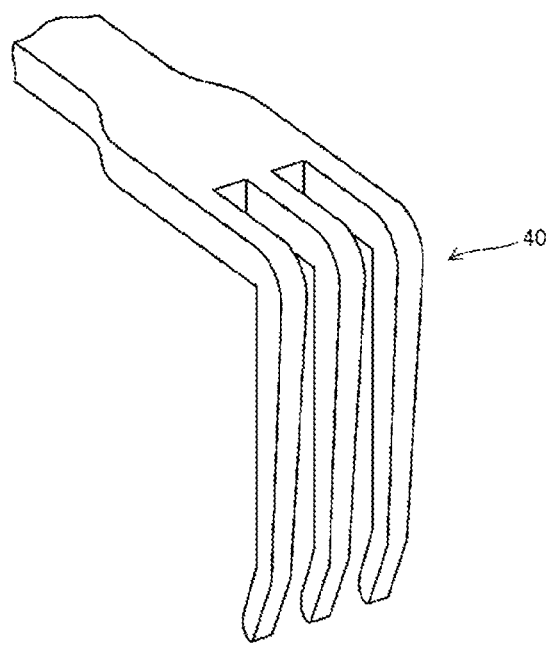
FIG. 12 is a view showing a modification of the shape of the hook-shaped portion.
Figure 13:
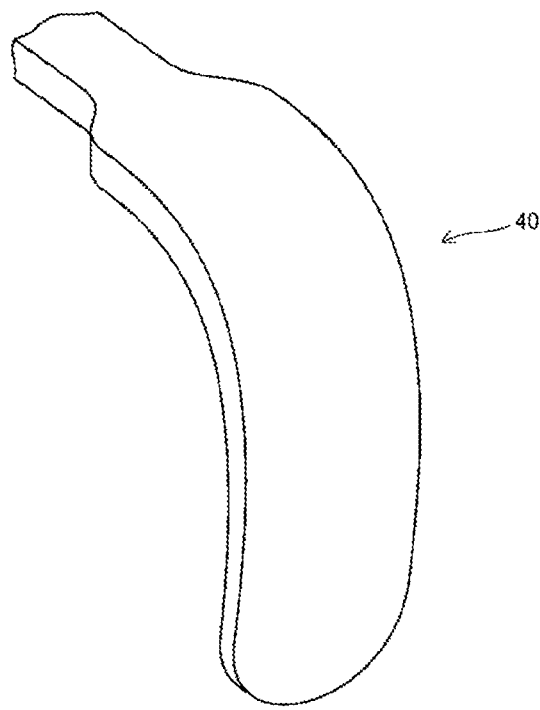
FIG. 13 is a view showing a modification of the shape of the hook-shaped portion.
Figure 14:
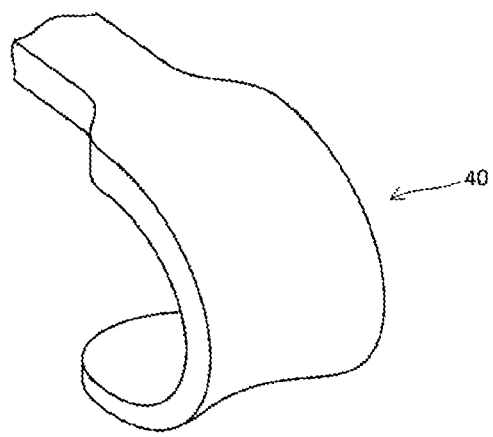
FIG. 14 is a view showing a modification of the shape of the hook-shaped portion.
Figure 15:
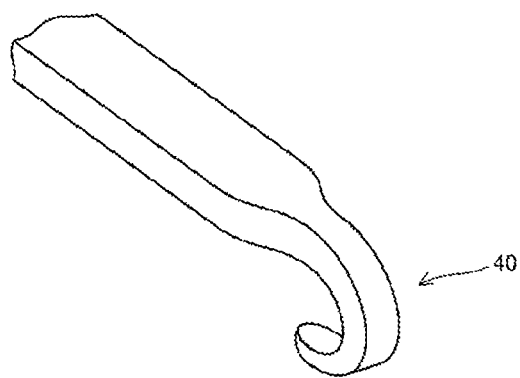
FIG. 15 is a view showing a modification of the shape of the hook-shaped portion.
Figure 16:
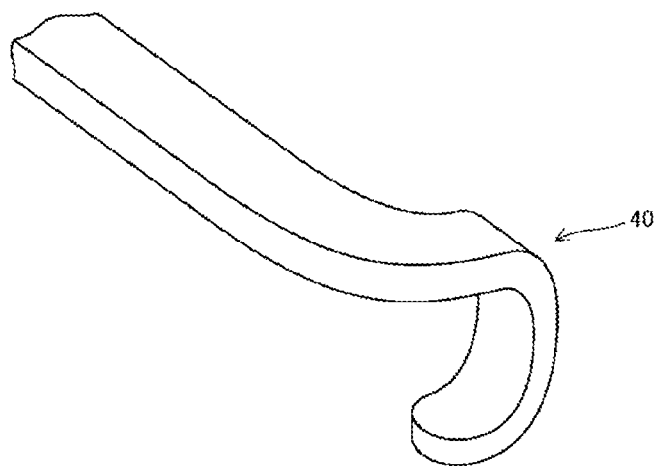
FIG. 16 is a view showing a modification of the shape of the hook-shaped portion.

FIG. 11 shows a hook-shaped portion 40 having a two-pronged shape at a distal end thereof, FIG. 12 shows a hook-shaped portion 40 having a three-pronged shape at a distal end thereof, and FIG. 13 shows a hook-shaped portion 40 having a larger width than a trunk portion 30 and being gently curved as a whole from a proximal end to a distal end of the hook-shaped portion 40. FIG. 14 shows a hook-shaped portion 40 having a larger width than a trunk portion 30 and being curved as a whole from a proximal end to a distal end thereof such that the distal end is directed toward a user's side, FIG. 15 shows a hook-shaped portion 40 having a narrower width than a trunk portion 30 and being curved as a whole from a proximal end to a distal end thereof such that the distal end is directed toward a user's side, and FIG. 16 shows a hook-shaped portion 40 which is formed by firstly bending the hook-shaped portion 40 sideward from the trunk portion 30, and secondly bending the hook-shaped portion 40 as a whole from a proximal end to a distal end thereof such that the distal end is directed to a user's side.

Modifications of the hook-shaped portion 40 shown in FIG. 11 to FIG. 16 are merely examples, and the medical retractors according to the present invention can adopt shapes substantially equal to shapes of existing various kinds of steel-made retractors or shapes of various kinds of steel-made retractors to be developed in the future as desired.

Figure 17:
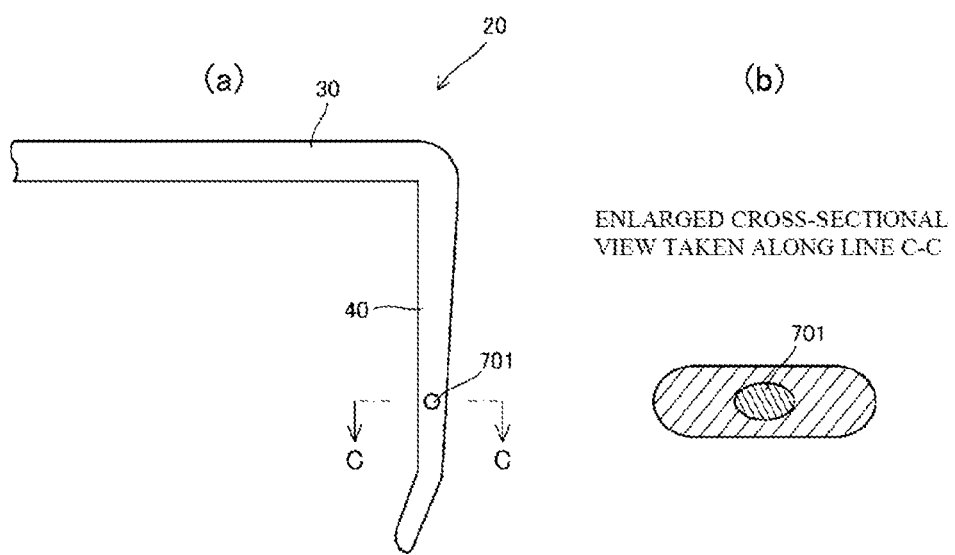
FIG. 17(a) and FIG. 17(b) are views showing a resin functional portion having a light storage member.

FIG. 17(a) and FIG. 17(b) are views showing a resin functional portion 20 including a light storage member 701. The resin functional portion 20 including the light storage member 701 can maintain a state where back-surface-side visibility and an affected part illuminating function of a resin functional portion 20 are enhanced due to emission of light from the light storage member 701 for a predetermined time even when the supply of power to the light source 12 is stopped. Further, light emitted from the light storage member 701 is superposed on leaked light from the resin functional portion 20 and light irradiated from the resin functional portion 20 and hence, the light storage member 701 also has an advantageous effect of increasing and stabilizing an amount of light.

Although FIG. 17(a) and FIG. 17(b) show the example where the light storage member 701 is embedded in a portion of the hook-shaped portion 40 in the vicinity of a distal end of the hook-shaped portion 40, the light storage member 701 may be disposed on other portions. The distal end of the hook-shaped portion 40 may be wholly formed of the light storage member 701 or any desired portion of the resin functional portion 20 may be formed of the light storage member 701.

FIG. 18(a) to FIG. 21(c) are views showing various modifications of the structure of the connecting portion 50.

In a connecting portion 50 shown in FIG. 18(a) to FIG. 18(c), an engaging and fixing portion 710 having a larger width than a trunk portion 30 is formed on a proximal end portion 30A of the trunk portion 30, and an engaging and fixing hole 711 into which the engaging and fixing portion 710 can be inserted is formed in a distal end of a grip portion 10. The engaging and fixing hole 711 differs in shape between an inlet portion 712 disposed in the vicinity of an inlet of the engaging and fixing hole 711 and a deep portion 713 on a depth side of the inlet.

That is, the inlet portion 712 is formed of an insertion hole having a shape obtained by integrating an angular hole which allows the engaging and fixing portion 710 to pass therethrough in a non-rotatable manner and a circular hole which allows the axial rotation of the trunk portion 30 with each other in a state where the centers of the respective holes are aligned with each other. The depth portion 713 is formed of a hole which allows the engaging and fixing portion 710 to rotate about an axis of the trunk portion 30 by a predetermined angle or more.

When the engaging and fixing portion 710 is inserted into the engaging and fixing hole 711 and reaches a depth end of the engaging and fixing hole 711, a shoulder portion 714 of the engaging and fixing portion 710 is just positioned at a boundary between the depth portion 713 and the inlet portion 712. When the trunk portion 30 is rotated about an axis in such a state, the shoulder portion 714 of the engaging and fixing portion 710 is brought into contact with and engaged with a stepped portion formed between the inlet portion 712 and the depth portion 713.

Figure 18:
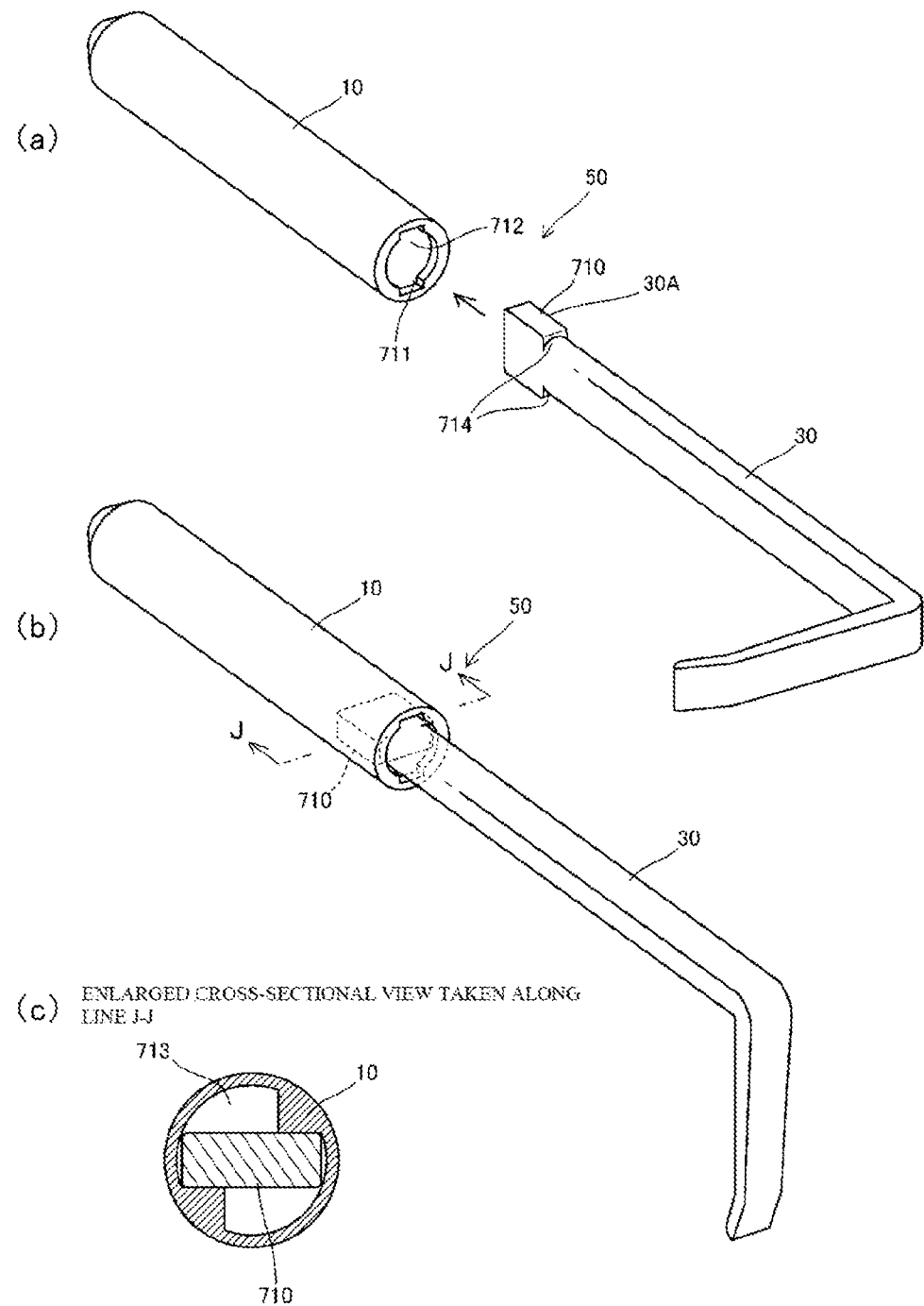
FIG. 18(a) to FIG. 18(c) are views showing a modification of the structure of the connecting portion.
Figure 19:
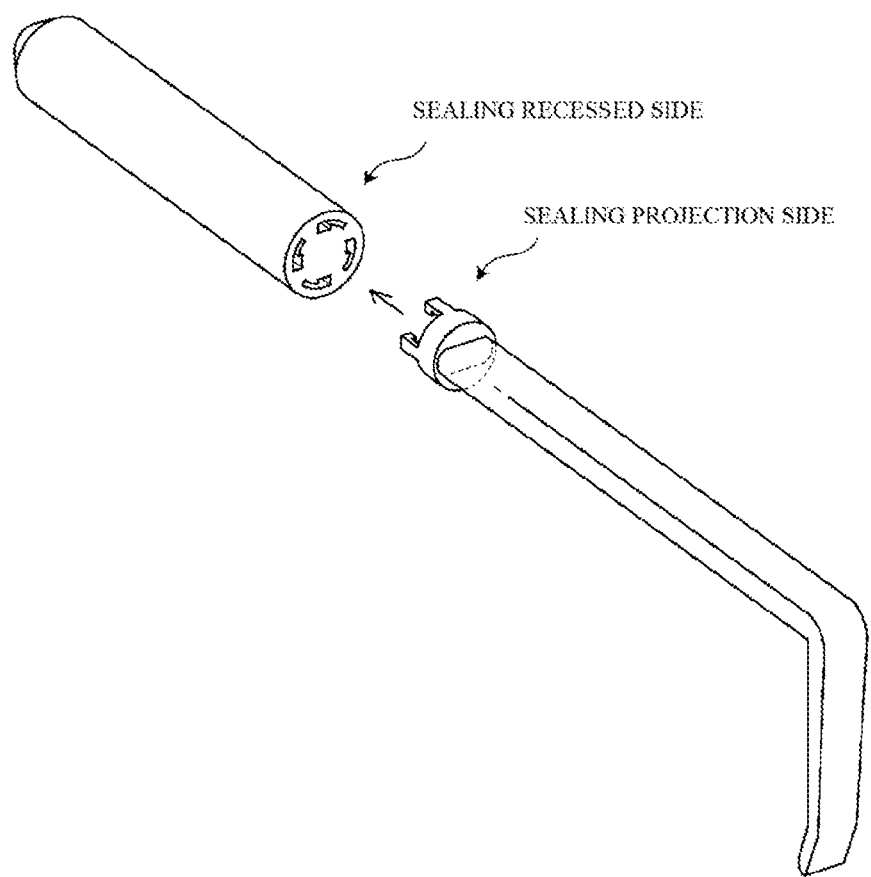
FIG. 19 is a view showing a modification of the structure of the connecting portion.

In this manner, according to the structure of the connecting portion 50 shown in FIG. 18, by merely inserting the engaging and fixing portion 710 into the engaging and fixing hole 711 and rotating the trunk portion 30 about the axis of the trunk portion 30, the resin functional portion 20 can be fixed to the grip portion 10. As a structure for fixing the resin functional portion 20 to the grip portion 10 by the insertion and the axial rotation of the trunk portion 30, various known structures can be named besides the above-mentioned structure. For example, an engaging structure substantially equal to a so-called ceiling light fixing structure shown in FIG. 19 may be adopted.

Figure 20:
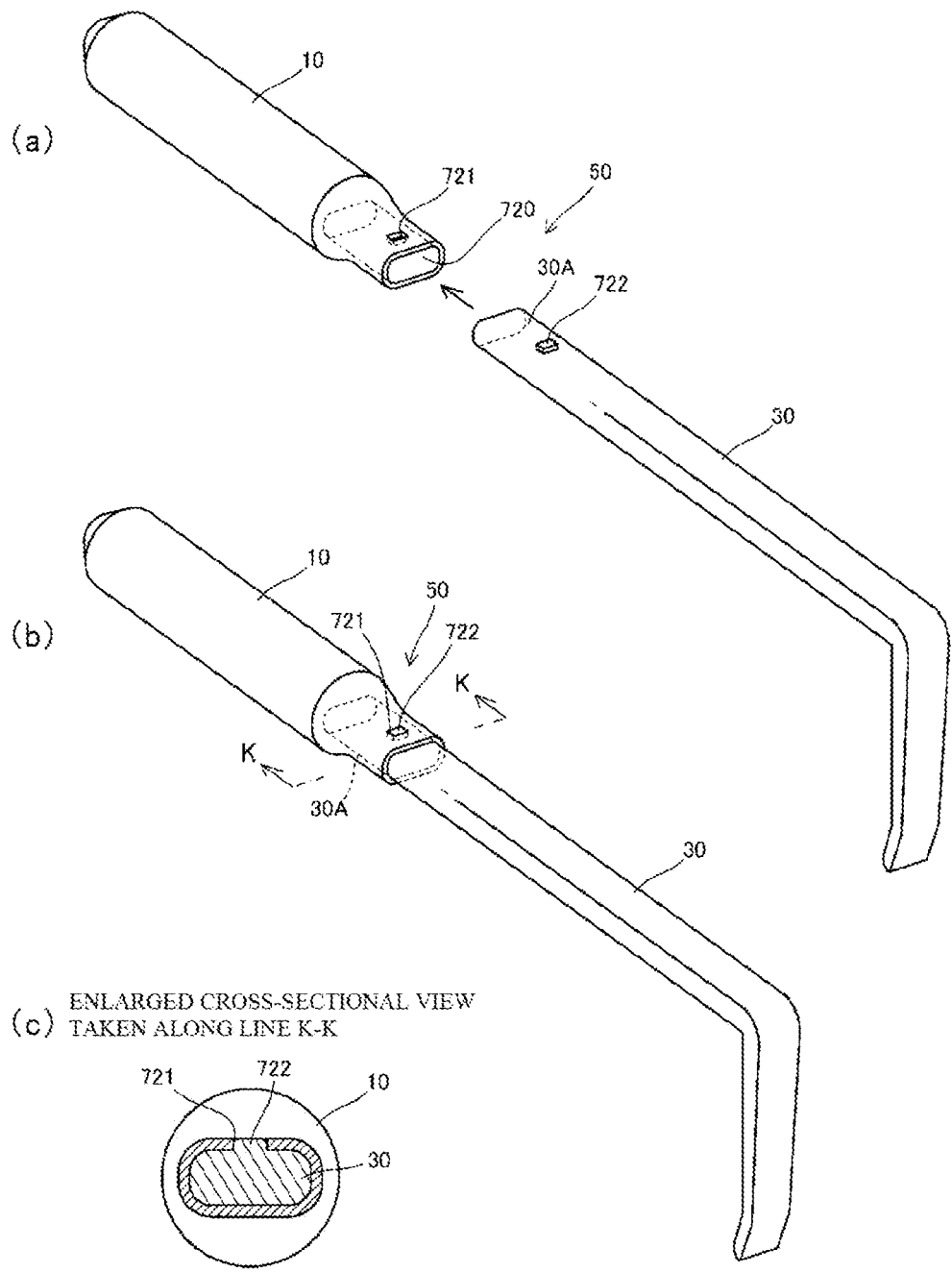
FIG. 20(a) to FIG. 20(c) are views showing a modification of the structure of the connecting portion.

Next, a connecting portion 50 shown in FIG. 20 is described. A size reduced portion 720 having substantially the same internal shape as an outer shape of a proximal end portion 30A of a trunk portion 30 is formed on a distal end of the grip portion 10, an engaging recessed portion 721 is formed in an inner wall surface of the size reduced portion 720, and an engaging projection 722 is formed on an outer wall surface of the trunk portion 30.

In this case, when the proximal end portion 30A of the trunk portion 30 is fitted in the size reduced portion 720, the engaging projection 722 is engaged with the engaging recessed portion 721 by concavo-convex fitting so that the trunk portion 30 is fixed to the grip portion 10. A plurality of engaging recessed portions 721 and a plurality of engaging projections 722 may be formed respectively.

Figure 21:
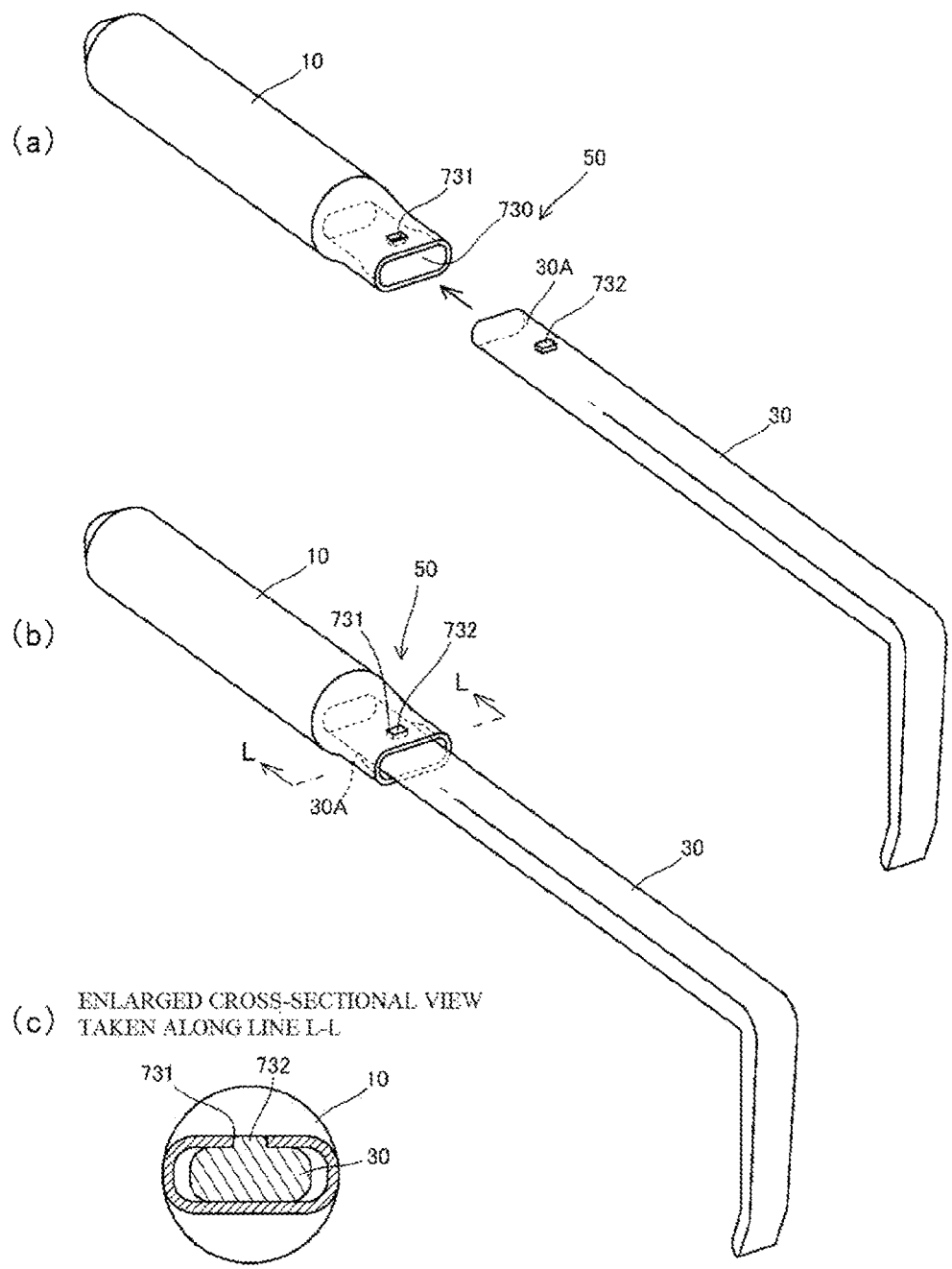
FIG. 21(a) to FIG. 21(c) are views showing a modification of the structure of the connecting portion.

Next, in a connecting portion 50 shown in FIG. 21, a size reduced portion 730 is formed on a distal end of a grip portion 10, and an inner shape of a depth portion of the size reduced portion 730 is set substantially equal to an outer shape of a proximal end portion 30A of a trunk portion 30. A portion of the size reduced portion 730 in the vicinity of an inlet has a larger width than the trunk portion 30 while having substantially the same thickness as the trunk portion 30. Further, an engaging recessed portion 731 is formed on the inner wall surface of the size reduced portion 730 in the vicinity of the inlet of the size reduced portion 730, and an engaging projection 732 is formed on the outer wall surface of the trunk portion 30.

In this case, when the proximal end portion 30A of the trunk portion 30 is inserted into the size reduced portion 730 and reaches a depth end of the size reduced portion 730, the engaging recessed portion 731 and the engaging projection 732 are engaged with each other by concavo-convex fitting so that the trunk portion 30 is fixed to the grip portion 10. Here, gaps are formed between both left and right side surfaces of the proximal end portion 30A of the trunk portion 30 and the size reduced portion 730.

In removing the trunk portion 30 from the grip portion 10, when a user presses and holds a portion of the grip portion 10 in the vicinity of the inlet of the size reduced portion 730 with a pressure in a width direction from the outside, the portion of the size reduced portion 730 in the vicinity of the inlet of the size reduced portion 730 bulges in the thickness direction due to elastic deformation so that the concavo-convex engagement between the engaging recessed portion 731 and the engaging projection 732 is released. Accordingly, the trunk portion 30 can be removed from the size reduced portion 730.

Figure 22:
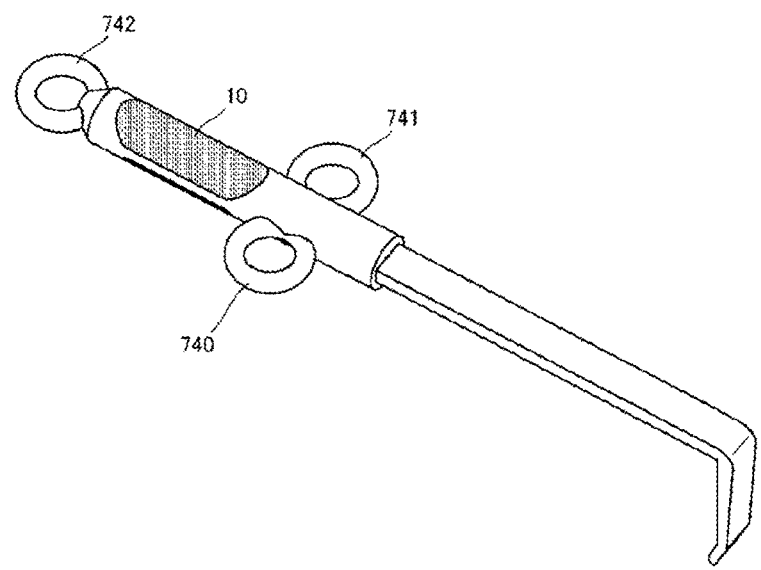
FIG. 22 is a view showing a modification of the grip portion.
Figure 23:
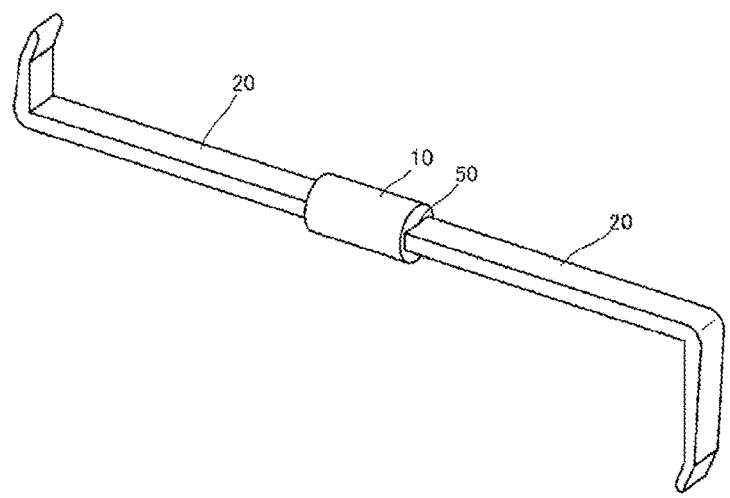
FIG. 23(a) and FIG. 23(b) are views showing a modification of the grip portion.
Figure 23:
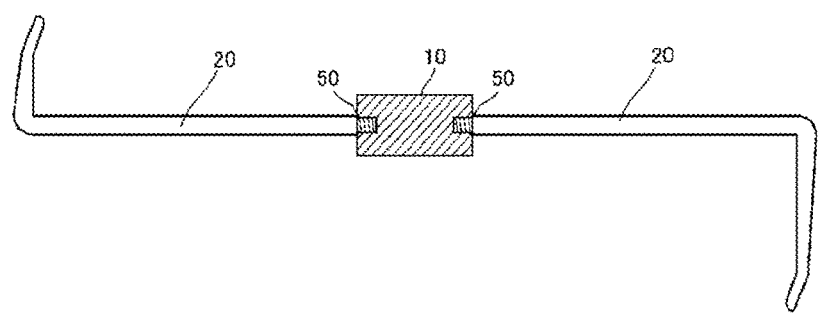

FIG. 22 and FIG. 23(a) and FIG. 23(b) are views showing various modifications of the grip portion 10.

As shown in FIG. 22, a grip portion 10 may have a finger hook structure on which a user can hook his fingers at the time of retracting a tissue near an affected part using a medical retractor. In FIG. 22, ring-shaped finger insertion holes 740, 741, 742 are formed in both left and right sides and a tail end of the grip portion 10. With the provision of such a finger hook structure, a burden applied to a doctor and an assistant during operation can be reduced. The portion where the finger hook structure is formed is not limited to the grip portion 10. The finger hook structure may be formed on the resin functional portion 20. In the case where the finger hook structure is formed on the resin functional portion 20, it is possible to apply a retracting force to the hook-shaped portion 40 used for retracting a tissue at the position closer to the hook-shaped portion 40.

As shown in FIG. 23(a) and FIG. 23(b), a grip portion 10 may be formed into a simple shape where neither a light source nor a power source is accommodated in the inside of the grip portion 10. With such a configuration, a medical retractor may be manufactured in a compact shape and the medical retractor may be light-weighted. Further, by providing a connecting portion 50 to both sides of the grip portion 10, medical instrument such as a resin functional portion 20 can be connected and fixed to both ends of the grip portion 10. In this case, a retractor which is connected to the side of the grip portion 10 opposite to the side of the grip portion to which a retractor used for retracting a tissue in the vicinity of an affected part is connected can be also used as an engaging structure for allowing a user to hook his fingers thereon at the time of retracting a tissue.

FIG. 24(a) and FIG. 24(b), and FIG. 25(a) and FIG. 25(b) are views showing modifications of the internal structure of the trunk portion 30 made of a resin.

Figure 24:
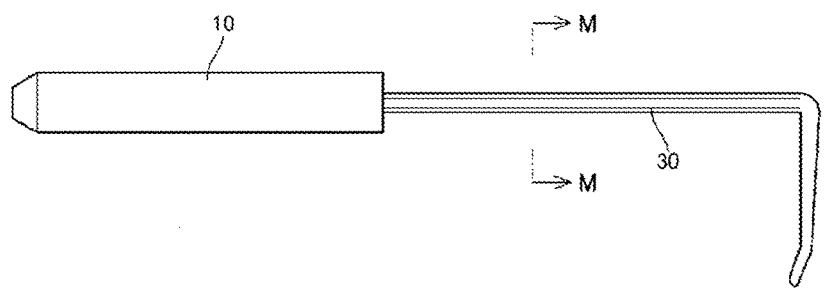
FIG. 24(a) and FIG. 24(b) are views showing a modification of the internal structure of a resin which forms a trunk portion.
Figure 24:
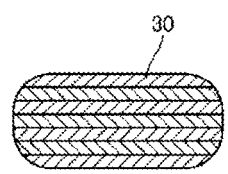
Figure 25:
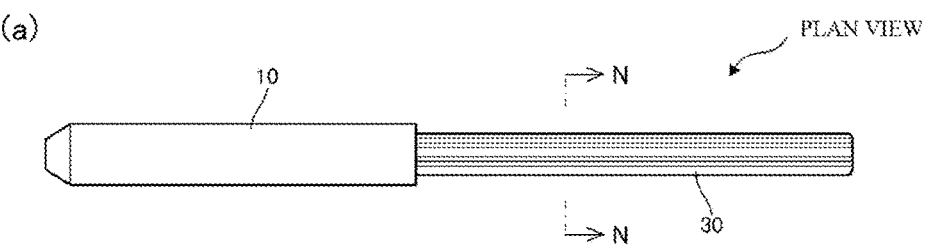
FIG. 25(a) and FIG. 25(b) are views showing a modification of the internal structure of the resin which forms the trunk portion.
Figure 25:
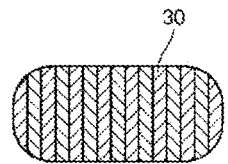

That is, the resin functional portion 20 may be configured to include a layered structure where layers are stacked on each other so as to have layer boundaries along an extending direction of the trunk portion 30. Such a layered structure can be obtained by forming the trunk portion 30 by stacking layers using a 3D printer or can be formed by insert molding. FIG. 24(a) and FIG. 24(b) show the layered structure having layer boundaries extending parallel to the front surface and the back surface of the trunk portion 30, and FIG. 25(a) and FIG. 25(b) show the layered structure having layer boundaries extending parallel to the right side surface and the left side surface of the trunk portion 30. By forming such layered structures, leaked light in a direction toward the layer boundaries from the resin functional portion 20 can be reduced thus enhancing the light guiding performance.

The present invention is not limited to the above-mentioned embodiments and modifications, and the present invention also includes: configurations acquired by replacing the respective constitutional elements disclosed in the above-mentioned embodiments and modifications with each other or by changing the combination of the above-mentioned constitutional elements; configurations acquired by replacing the respective constitutional elements disclosed in known techniques, the above-mentioned embodiments and modifications with each other or by changing the combination of the above-mentioned constitutional elements; and the like. Further, the technical scope of the present invention is not limited to the above-mentioned embodiments, and covers matters described in Claims and matters considered equivalent to the matters described in Claims.

REFERENCE SIGNS LIST

1: medical retractor, 10: grip portion, 11: accommodating space, 12: light source, 13: power source, 20: resin functional portion, 30: trunk portion, 30A: proximal end portion, 30B: distal end portion, 31: front surface, 34: back surface, 40: hook-shaped portion, 41: front surface, 42: right side surface, 43: left side surface, 44: back surface, 45: distal end surface, 50: connecting portion, 60: bent portion, 200: medical retractor, 231: front surface, 234: back surface, 241: front surface, 244: back surface, 300: medical retractor, 370: ridge, 371: first portion, 372: second portion, 400: medical retractor, 470: light guiding portion, 471: first portion, 472: second portion, 500: medical retractor, 570: light guiding portion, 600A: medical retractor, 600B: medical retractor, 660: prism structure, 670: light reflection portion, 701: light storage member, 710: engaging and fixing portion, 711: engaging and fixing hole, 712: inlet portion, 713: depth portion, 714: shoulder portion, 720: recessed portion, 721: engaging indent, 722: engaging projection, 730: size reduced portion, 731: engaging recessed portion, 732: engaging projection, 740: finger insertion hole, 741: finger insertion hole, 742: finger insertion hole, 800: medical retractor, 810: grip portion, 811: barrel portion, 812: right finger hook portion, 813: left finger hook portion, 814: rear finger hook portion, 815: switch, 816: connecting portion, 816a: female threaded structure, 816b: male threaded structure, 817: distal end side barrel portion, 817a: end surface, 817b: stepped portion, 818: tail end side barrel portion, 818a: end surface, 818b: stepped portion, 819: groove, 820: resin functional portion, 830: trunk portion, 830A: proximal end portion, 830B: distal end portion, 831: front surface, 834: back surface, 835: ridge, 840: hook-shaped portion, 841: front surface, 842: right side surface, 843: left side surface, 844: back surface, 845: distal end portion, 850: connecting portion, 851: male threaded structure, 852: recessed portion, 853: female threaded structure, 854: end surface, 855: end surface, 860: bent portion, 861: front surface, 864: back surface, 870: accommodating space, 871: hole, 872: cap-shaped part, 873: printed circuit board, 874: reflector, 875: light source, 876: power source, 880: rotation amount regulation means, 890: rotation amount regulation means, 881: engaging projection, 882: engaging recessed portion, 900: medical retractor, 910: grip portion

The invention claimed is:

1. A medical retractor comprising:
a grip portion; and
a resin functional portion made of a transparent resin and extending from the grip portion, wherein
the resin functional portion has: a trunk portion which has a proximal end thereof connected to the grip portion; and a hook-shaped portion extending in a hook shape from a distal end of the trunk portion,
the resin functional portion is configured to allow the viewing of an affected part which opposedly faces a back surface of the resin functional portion from a front surface side in a see-through manner,
the resin functional portion is configured such that at least one of the back surface and the front surface has a convex lens shape, and
the resin functional portion has a projection extending to the hook-shaped portion along the front surface of the resin functional portion, and the projection formed on the hook-shaped portion is formed with a larger width and a smaller projecting height compared to the projection formed in the trunk portion.

2. The medical retractor according to claim 1, wherein the grip portion incorporates a light source which emits light by a power source therein such that the light from the light source is incident on the proximal end of the trunk portion and is transmitted toward the hook-shaped portion whereby visibility of a tissue of the affected part which opposedly faces the back surface of the resin functional portion from the front surface side of the resin functional portion is enhanced.

3. The medical retractor according to claim 2, wherein the grip portion is configured such that a communication passage between a fixing hole in which the resin functional portion is fixed and an accommodating space in which the light source is accommodated are sealed by a sealing material.

4. The medical retractor according to claim 2, wherein the resin functional portion includes a layered structure where layers are stacked so as to have a layer boundary along an extending direction of the trunk portion.

5. The medical retractor according to claim 1, wherein the back surface and the front surface of the resin functional portion respectively comprise a flat surface.

6. The medical retractor according to claim 1, wherein at least one of water repellant finish or oil repellant finish is applied to a surface of the resin functional portion.

7. The medical retractor according to claim 1, wherein a portion of the hook-shaped portion is formed of a light storage member.

8. The medical retractor according to claim 1, wherein a prism structure which makes light refract and advance is disposed at a bent portion between the trunk portion and the hook-shaped portion.

9. The medical retractor according to claim 1, wherein a reflection portion is formed along an outer peripheral surface of a bent portion between the trunk portion and the hook-shaped portion.

10. The medical retractor according to claim 1, wherein finger hooking structures which project sideward from side surfaces of the grip portion are provided in left and right symmetry.

* * * * *